United States Patent
Kojima

(10) Patent No.: US 12,133,637 B2
(45) Date of Patent: Nov. 5, 2024

(54) MEDICAL OBSERVATION SYSTEM

(71) Applicant: Sony Olympus Medical Solutions Inc., Tokyo (JP)

(72) Inventor: Koji Kojima, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 286 days.

(21) Appl. No.: 16/978,768

(22) PCT Filed: Jan. 10, 2019

(86) PCT No.: PCT/JP2019/000598
§ 371 (c)(1),
(2) Date: Sep. 8, 2020

(87) PCT Pub. No.: WO2019/176253
PCT Pub. Date: Sep. 19, 2019

(65) Prior Publication Data
US 2020/0405135 A1   Dec. 31, 2020

(30) Foreign Application Priority Data
Mar. 15, 2018  (JP) .................................. 2018-047944

(51) Int. Cl.
*A61B 1/06* (2006.01)
*A61B 1/00* (2006.01)
*A61B 1/045* (2006.01)

(52) U.S. Cl.
CPC ........ *A61B 1/0638* (2013.01); *A61B 1/00045* (2013.01); *A61B 1/00186* (2013.01);
(Continued)

(58) Field of Classification Search
CPC ............ A61B 1/00039; A61B 1/00045; A61B 1/00186; A61B 1/063; A61B 1/0655; A61B 1/045; A61B 1/00009; A61B 1/043
See application file for complete search history.

(56) References Cited

U.S. PATENT DOCUMENTS 4,931,867 A * 6/1990 Kikuchi .................... A61B 1/05
348/E5.025
5,262,849 A * 11/1993 Mimura ............. H04N 9/04515
348/224.1
(Continued)

FOREIGN PATENT DOCUMENTS

JP          06304135 A  *  4/1993
JP          11-104074 A      4/1999
(Continued)

OTHER PUBLICATIONS

Machine Language Translation of JP-06304135-A to Komatsu (Apr. 1993) (Year: 1993).*
(Continued)

*Primary Examiner* — John P Leubecker
*Assistant Examiner* — Jae Woo
(74) *Attorney, Agent, or Firm* — XSENSUS LLP

(57) ABSTRACT

A medical observation system according to the present invention includes: an observation optical system configured to guide an observation light from a subject; an imaging unit configured to receive an observation light from the observation optical system and generate an image signal; and an image processing unit configured to apply signal processing to the image signal generated by the imaging unit, wherein the image processing unit includes a filter detection unit configured to detect, based on a signal value of a color which includes a wavelength band of a specific light in a preset wavelength band of the image signal, whether or not an observation-side filter for cutting the specific light is disposed on an optical path of the observation light.

23 Claims, 17 Drawing Sheets

(52) U.S. Cl.
CPC ............ *A61B 1/045* (2013.01); *A61B 1/0655* (2022.02); *A61B 1/000095* (2022.02)

(56) References Cited

U.S. PATENT DOCUMENTS

| | | | | |
|---|---|---|---|---|
| 5,267,028 | A * | 11/1993 | Suga | H04N 9/735 |
| | | | | 348/251 |
| 5,408,263 | A * | 4/1995 | Kikuchi | A61B 1/05 |
| | | | | 348/370 |
| 5,647,368 | A * | 7/1997 | Zeng | A61B 5/42 |
| | | | | 600/476 |
| 5,749,830 | A * | 5/1998 | Kaneko | A61B 1/00186 |
| | | | | 348/E5.038 |
| 6,099,466 | A * | 8/2000 | Sano | A61B 1/0646 |
| | | | | 600/109 |
| 2003/0151681 | A1 * | 8/2003 | Miyahara | H04N 9/04561 |
| | | | | 348/254 |
| 2004/0143157 | A1 * | 7/2004 | Doguchi | A61B 1/0638 |
| | | | | 348/E3.018 |
| 2006/0178565 | A1 * | 8/2006 | Matsui | A61B 1/0655 |
| | | | | 600/109 |
| 2009/0012361 | A1 * | 1/2009 | MacKinnon | A61B 1/043 |
| | | | | 600/118 |

FOREIGN PATENT DOCUMENTS

| | | |
|---|---|---|
| JP | 2003-235786 A | 8/2003 |
| JP | 2016-198634 A | 12/2016 |

OTHER PUBLICATIONS

International Search Report and Written Opinion dated Mar. 26, 2019 for PCT/JP2019/000598 filed on Jan. 10, 2019, 6 pages including English Translation of the International Search Report.

* cited by examiner

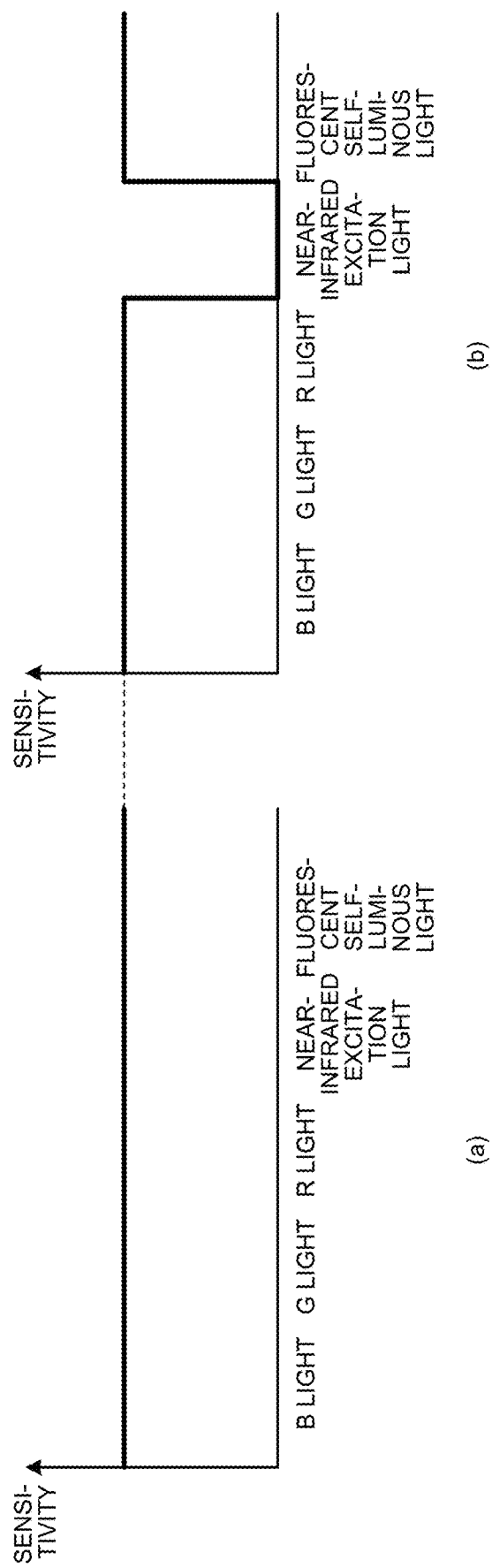

MEDICAL OBSERVATION SYSTEM

CROSS-REFERENCE TO RELATED APPLICATIONS

The present application is based on PCT filing PCT/JP2019/000598, filed Jan. 10, 2019, which claims priority to JP 2018-047944, filed Mar. 15, 2018, the entire contents of each are incorporated herein by reference.

FIELD

The present invention relates to a medical observation system.

BACKGROUND

In recent years, there has been proposed an observation method where special light observation using special light is performed separately from normal observation using white light. Specifically, as special light observation, a technique referred to as an NBI (Narrow Band Imaging), a technique referred to as an IRI (Infra-Red Imaging), a technique referred to as an AFI (Auto Fluorescence Imaging), a technique referred to as a PDD (Photodynamic Diagnosis) and the like may be named.

In the technique referred to as the NBI, a narrow-band illumination light having wavelengths of 415 nm and 540 nm as central wavelengths is irradiated, and a state of blood vessels in a mucosa surface layer and a state of blood vessels in the deeper layer are observed by making use of the difference in absorption of light of each wavelength with respect to hemoglobin. The light of 415 nm is absorbed by hemoglobin in the mucosa surface layer, and the light of 540 nm is absorbed by hemoglobin in a slightly deeper layer.

In the technique referred to as the IRI, a chemical agent referred to as indocyanine green (ICG) which has an absorption peak in near-infrared light having a wavelength of approximately 805 nm in blood is intravenously injected as a contrast agent, and near-infrared lights having a central wavelength of 805 nm and a central wavelength of 940 nm are irradiated, a shade of a blood vessel part of a submucosal layer formed by the absorption of ICG is observed thus performing diagnoses of a running state of blood vessels and a running state of lymphatic vessels. In the technique referred to as the IRI, intensity of a light having a central wavelength of 805 nm changes depending on the presence or absence of a tumor.

In the technique referred to as the AFI, by pre-administering a fluorescent agent into a subject and by irradiating an excitation light to the subject, a fluorescence image emitted from the subject is observed, and the presence or absence and a shape of the fluorescence image are observed thus performing a diagnosis of a tumor part. In normal tissues, fluorescence is emitted from the fluorescent agent on the mucosa surface layer, and when the accumulation of blood vessels and an increase of a thickness of mucosa occur on the mucosa surface layer due to a lesion, the fluorescence from a phosphor is remarkably reduced.

In the technique referred to as the PDD, when a solution in which an aminolevulinic acid (5-ALA) is dissolved is administered to a patient, the solution is metabolized into a blood material (heme) in normal tissues in the body. However, the solution is not metabolized in cancer cells and is accumulated as a substance referred to as an intermediate product PpIX. When a blue light (center wavelength 410 nm) is irradiated to the PpIX, the PpIX emits fluorescence in red (peak wavelength 630 nm). By making use of such properties of the normal tissues and the cancer cells, it is possible to obtain an image by which the cancer cells may be easily distinguished from the normal cells. The normal cells emit a blue light by receiving an irradiated blue light, for example, a light of 460 nm at a foot of the irradiated blue light.

When a special light observation is performed, for example, when the IRI, the AFI or the PDD is performed, an excitation light which excites a fluorescent pigment or a fluorescent label is irradiated. In this case, the observation optical system includes, to prevent the occurrence of a phenomenon that a subject reflects an excitation light and a reflected light is incident on an image sensor, a filter which cuts a light in an excitation wavelength band (for example, see Patent Literature 1).

CITATION LIST

Patent Literature

Patent Literature 1: JP 2016-198634 A

SUMMARY

Technical Problem

In performing a special light observation, it is necessary to arrange the above-mentioned filter in the observation optical system. Accordingly, it is desirable to detect the presence or absence of the filter in the observation optical system. Conventionally, there has been known a technique where a detection block is provided for detecting a type of a rigid endoscope by detecting a mask shape of an eyepiece of the rigid endoscope. However, the provision of the detection block increases the scale of a circuit.

The present invention has been made in view of the above-mentioned circumstances, and it is an object of the present invention to provide a medical observation system capable of detecting the presence or absence of a filter in an observation optical system while suppressing the increase of the scale of a circuit.

Solution to Problem

To solve the above-described problem and achieve the object, a medical observation system according to the present invention includes: an observation optical system configured to guide an observation light from a subject; an imaging unit configured to receive an observation light from the observation optical system and generate an image signal; and an image processing unit configured to apply signal processing to the image signal generated by the imaging unit, wherein the image processing unit includes a filter detection unit configured to detect, based on a signal value of a color which includes a wavelength band of a specific light in a preset wavelength band of the image signal, whether or not an observation-side filter for cutting the specific light is disposed on an optical path of the observation light.

Moreover, in the above-described medical observation system according to the present invention, the observation-side filter is insertable into and removable from the optical path of the observation light.

Moreover, the above-described medical observation system according to the present invention further includes an input unit configured to receive an input of an instruction from an outside, and the filter detection unit is configured to perform detection processing of the observation-side filter when a white balance adjustment processing instruction is inputted to the input unit.

Moreover, the above-described medical observation system according to the present invention further includes a control unit configured to control, based on a detection result of the filter detection unit, a display device and/or an output unit to perform notification processing indicating that the observation-side filter is not provided when it is determined that the observation-side filter does not exist on the optical path of the observation light based on a detection result of the filter detection unit.

Moreover, the above-described medical observation system according to the present invention further includes a light source unit configured to emit an illumination light which includes at least the specific light.

Moreover, the above-described medical observation system according to the present invention further includes a light source controller configured to control, based on a detection result of the filter detection unit, emission of the illumination light from the light source unit when it is determined that the observation-side filter does not exist on the optical path of the observation light.

Advantageous Effects of Invention

According to the present invention, it is possible to acquire an advantageous effect that the presence or absence of a filter in the observation optical system may be detected while suppressing the increase of the scale of a circuit.

BRIEF DESCRIPTION OF DRAWINGS

FIG. 4 is a view for explaining sensitivity of an observation-side filter provided during the special light observation in the endoscope device according to the first embodiment.

DESCRIPTION OF EMBODIMENTS

Hereinafter, modes for carrying out the present invention (hereinafter, referred to as "embodiments") are described. In the embodiments, the description is made with respect to a medical endoscope device which captures and displays an image inside a subject such as a patient as an example of a medical observation system according to the present invention. However, the present invention is not limited to the following embodiments. In the description of the drawings, the description is made by giving the same symbols to identical portions.

First Embodiment

Figure 1:
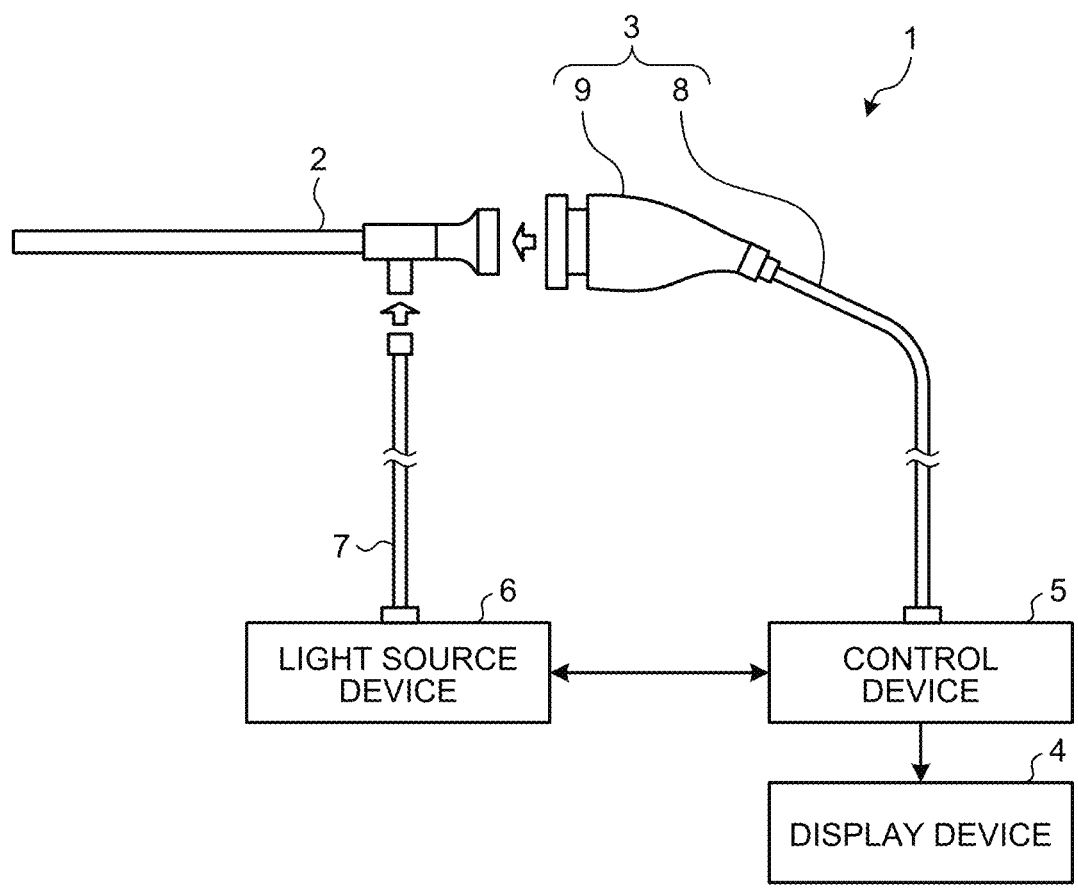
FIG. 1 is a view illustrating a schematic configuration of an endoscope device according to a first embodiment of the present invention.

FIG. 1 is a view illustrating the schematic configuration of an endoscope device 1 according to a first embodiment of the present invention. The endoscope device 1 is a device which is used in medical fields and is used for observing a subject in an observation target such as a person (inside a living body). As illustrated in FIG. 1, the endoscope device 1 includes an endoscope 2, an imaging device 3, a display device 4, a control device 5 (image processing device), and a light source device 6. The imaging device 3 and the control device 5 form a medical observation system. In the first embodiment, the endoscope 2 and the imaging device 3 form an image acquisition device which uses an endoscope such as a rigid endoscope, for example.

The light source device 6 includes: a light source unit 61 to which one end of a light guide 7 is connected and which supplies an illumination light such as a white light for illuminating the inside of a living body or a near-infrared light used for special observation or the like to one end of the light guide 7; and a light source controller 62 for controlling emission of an illumination light from the light source unit 61. The light source unit 61 includes: an illumination optical system which emits an illumination light, and an illumination-side filter which is insertably and removably disposed in an optical path of the illumination light. The illumination-side filter operates under a control of the light source controller 62. As illustrated in FIG. 1, the light source device 6 and the control device 5 may be formed as separate bodies which are communicable with each other. The light source device 6 and the control device 5 may be formed as an integral body.

One end of the light guide 7 is detachably connected to the light source device 6 and the other end of the light guide 7 is detachably connected to the endoscope 2. The light guide 7 transmits a light supplied from the light source device 6 from the one end to the other end thereof and supplies the light to the endoscope 2.

The imaging device 3 captures a subject image from the endoscope 2 and outputs the imaging result. As illustrated in FIG. 1, the imaging device 3 includes: a transmission cable 8 which is a signal transmission unit; and a camera head 9. In the first embodiment, the transmission cable 8 and the camera head 9 form a medical imaging device.

The endoscope 2 is rigid and has an elongated shape, and is inserted into a living body. In the endoscope 2, an observation optical system which is formed of one or a plurality of lenses and focuses a subject image is disposed. The endoscope 2 emits a light supplied through the light guide 7 from a distal end of the endoscope 2 and irradiates the light to the inside of a living body. The light (subject image) irradiated to the inside of the living body is focused by the observation optical system (lens unit 91) in the endoscope 2. In the first embodiment, as described later, the endoscope 2 has the configuration where a filter which cuts a light in a predetermined wavelength band (hereinafter referred to as an observation-side filter) is provided, and a configuration where the observation-side filter is not provided. For example, in a case where the light source device 6 emits a light in a near-infrared wavelength band, the observation-side filter cuts a light in the near-infrared wavelength band.

The camera head 9 is detachably connected to a proximal end of the endoscope 2. Under the control of the control device 5, the camera head 9 captures a subject image focused by the endoscope 2, and outputs an imaging signal obtained by imaging. The detailed configuration of the camera head 9 is described later. The endoscope 2 and the camera head 9 may be configured in a detachable manner as illustrated in FIG. 1, or the endoscope 2 and the camera head 9 may be formed as an integral body.

One end of the transmission cable 8 is detachably connected to the control device 5 via a connector, and the other end of the transmission cable 8 is detachably connected to the camera head 9 via a connector. Specifically, the transmission cable 8 is a cable where a plurality of electrical wires (not illustrated) are disposed in an outer cover which forms an outermost layer. The plurality of electrical wires are electric wires for transmitting an imaging signal outputted from the camera head 9 to the control device 5, and for transmitting a control signal, a synchronizing signal, a clock, and power outputted from the control device 5 to the camera head 9 respectively.

The display device 4 displays an image generated by the control device 5 under the control of the control device 5. It is preferable that the display device 4 have a display unit having a size of 55 inches or more in order to make a viewer immerse himself or herself in the display unit during observation. However, the size of the display unit is not limited to such a size.

The control device 5 processes an imaging signal inputted from the camera head 9 via the transmission cable 8, outputs an image signal to the display device 4, and controls an operation of the camera head 9 and the display device 4 in a comprehensive manner. The detailed configuration of the control device 5 is described later.

Figure 2:
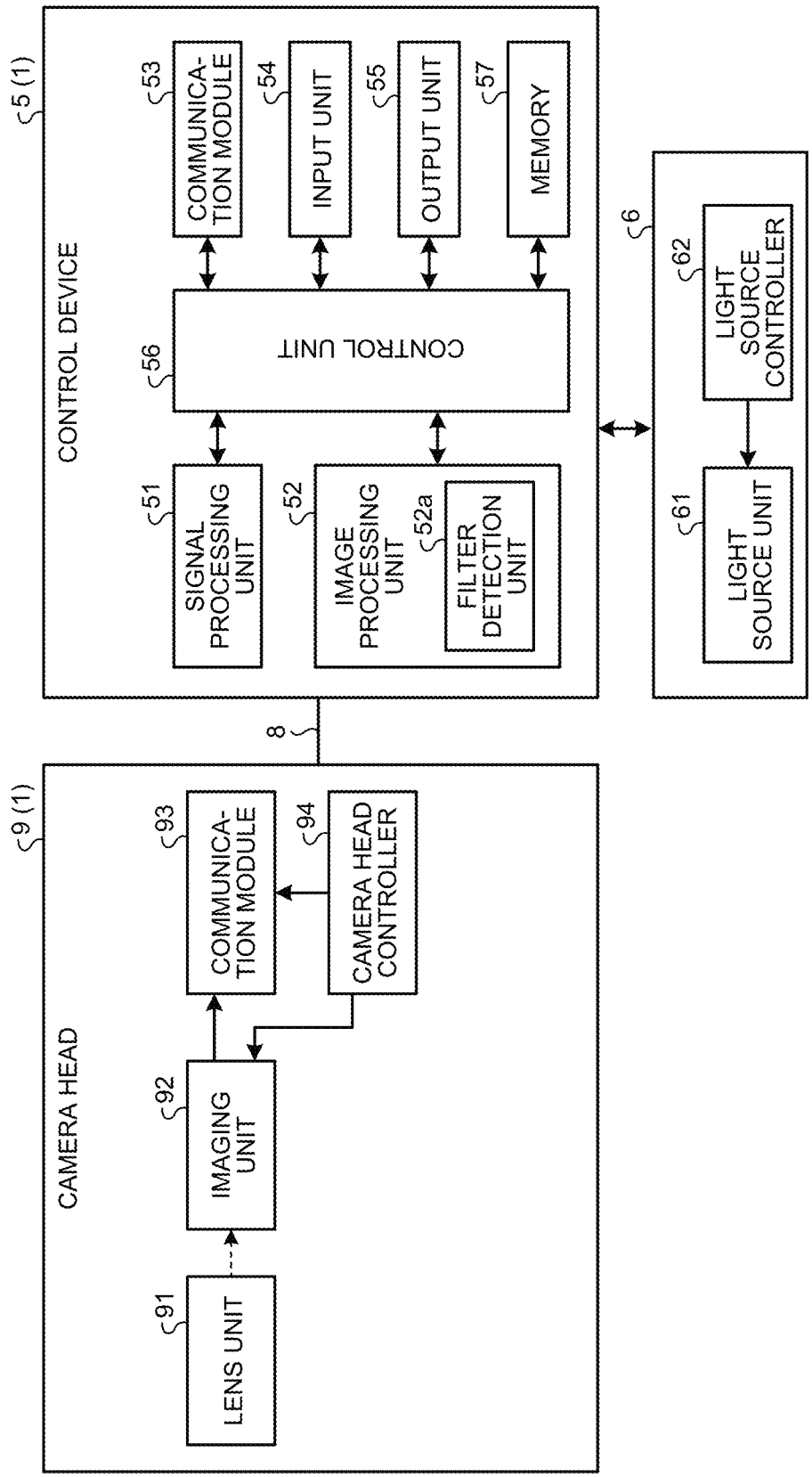
FIG. 2 is a block diagram illustrating the configuration of a camera head and the configuration of a control device illustrated in FIG. 1.

Next, the configuration of the imaging device 3 and the configuration of the control device 5 are described. FIG. 2 is a block diagram illustrating the configuration of the camera head 9 and the configuration of the control device 5. In FIG. 2, the illustration of a connector which detachably connects the camera head 9 and the transmission cable 8 to each other is omitted.

Hereinafter, the configuration of the control device 5 and the configuration of the camera head 9 are described in this order. Hereinafter, with respect to the configuration of the control device 5, constitutional elements which form a main part of the present invention are mainly described. As illustrated in FIG. 2, the control device 5 includes a signal processing unit 51, an image processing unit 52, a communication module 53, an input unit 54, an output unit 55, a control unit 56, and a memory 57. The control device 5 may include a power source unit (not illustrated) or the like which generates a power source voltage for driving the control device 5 and the camera head 9, supplies the generated power source voltage to respective portions of the control device 5 and, at the same time, supplies the generated power source voltage to the camera head 9 via the transmission cable 8.

The signal processing unit 51 outputs digitized imaging signals (pulse signals) to the image processing unit 52 by removing noises from imaging signals which the camera head 9 outputs and by performing signal processing such as A/D conversion when necessary.

The signal processing unit 51 generates synchronizing signals and clocks for the imaging device 3 and the control device 5. A synchronizing signal (for example, a synchronizing signal for instructing an imaging timing of the camera head 9) to the imaging device 3 and a clock (for example, a clock for serial communication) are transmitted to the imaging device 3 via lines not illustrated, and the imaging device 3 is driven based on the synchronizing signal and the clock.

The image processing unit 52 generates a display image signal for a display displayed by the display device 4 based on an imaging signal inputted from the signal processing unit 51. The image processing unit 52 generates a display image signal including a subject image by executing predetermined signal processing with respect to the imaging signal. The image processing unit 52 performs known various image processing such as detection processing, interpolation processing, color correction processing, color emphasis processing, and contour emphasis processing. The image processing unit 52 outputs a generated image signal to the display device 4.

The image processing unit 52 also includes a filter detection unit 52*a* which detects whether or not a filter for cutting light in a predetermined wavelength band is inserted in the optical path based on an imaging signal. The detail of the filter detection processing by the filter detection unit 52*a* is described later.

The communication module 53 outputs a signal from the control device 5 which includes a control signal described later transmitted from the control unit 56 to the imaging device 3. The communication module 53 outputs a signal from the imaging device 3 to the respective parts in the control device 5. That is, the communication module 53 is a relay device which collectively outputs signals from the respective parts of the control device 5 which are outputted to the imaging device 3 by parallel-to-serial conversion or the like, for example, and outputs signals inputted from the imaging device 3 to the respective parts of the control device 5 by distributing the signals by serial-to-parallel conversion or the like, for example.

The input unit 54 is realized by using a user interface such as a keyboard, a mouse, and a touch panel, and receives inputting of various information.

The output unit 55 is realized by using a speaker, a printer, a display or the like, and outputs various information. The output unit 55 performs outputting of an alarm sound and an alarm light and an image display under the control of the control unit 56. For example, in a case where it is determined that the observation-side filter is not inserted in the optical path based on a detection result from the filter detection unit 52*a*, the output unit 55 outputs an alarm sound or an alarm light under the control of the control unit 56.

The control unit 56 performs a drive control of the respective components including the control device 5 and the camera head 9, and an input/output control of information with respect to the respective components, and other controls. The control unit 56 generates a control signal by looking up communication information data (for example, communication format information or the like) stored in the memory 57, and transmits the generated control signal to the imaging device 3 via the communication module 53. The control unit 56 outputs a control signal to the camera head 9 via the transmission cable 8. The control unit 56 switches a wavelength band of an illumination light which the light source device 6 emits in accordance with an instruction for switching an observation method inputted via the input unit 54, for example. As the observation method, the normal observation where a white light is emitted and the special light observation where a light in a wavelength band different from the white wavelength band is emitted are named. In the first embodiment, the IRI observation where the fluorescence of indocyanine green is observed by emitting a light in a near-infrared wavelength band is described as an example of the special light observation.

The memory 57 is realized using a semiconductor memory such as a flash memory or a dynamic random access memory (DRAM). In the memory 57, communication information data (for example, format information for communication or the like) is stored. In the memory 57, various programs executed by the control unit 56 may be stored.

The signal processing unit 51 may include: an AF processing unit which outputs a predetermined AF evaluation value for each frame based on an imaging signal inputted to the frame; and an AF calculation unit which performs AF calculation processing for selecting a frame or a focus lens position most suitable as a focus position based on the AF evaluation values for the respective frames from the AF processing unit.

The above-described signal processing unit 51, the image processing unit 52, the communication module 53, and the control unit 56 are realized by using a general-purpose processor such as a central processing unit (CPU) having an internal memory (not illustrated) in which a program is stored, or a dedicated processor such as various arithmetic operation circuits which perform specific function such as an Application Specific Integrated Circuit (ASIC). The above-described parts may be formed by using a Field Programmable Gate Array (FPGA, not illustrated) which is a kind of programmable integrated circuit. In a case where the above-mentioned parts are formed of the FPGA, a memory for storing configuration data may be provided so that the FPGA which is a programmable integrated circuit may be configurated based on the configuration data read from the memory.

Next, the description is made mainly with respect to the configuration of the camera head 9 as an essential part of the present invention. As illustrated in FIG. 2, the camera head 9 includes a lens unit 91, an imaging unit 92, a communication module 93, and a camera head controller 94. In the first embodiment, as described later, the camera head 9 has: the configuration where an observation-side filter which cuts a light in a predetermined wavelength band; and the configuration where such a filter is not provided.

The lens unit 91 is formed of one or a plurality of lenses, and focuses a subject image which has passed the lens unit 91 on an imaging screen of an image sensor which forms the imaging unit 92. The above-mentioned one or a plurality of lenses are movable along an optical axis. The lens unit 91 includes an optical zoom mechanism (not illustrated) which changes an angle of an image and a focusing mechanism which changes a focal position by moving the above-mentioned one or a plurality of lenses. The lens unit 91 also forms an observation optical system which guides an observation light incident on the endoscope 2 to the imaging unit 92 together with the optical system disposed in the endoscope 2.

The imaging unit 92 captures a subject image under the control of the camera head controller 94. The imaging unit 92 is formed of an image sensor which receives a subject image imaged by the lens unit 91 and converts the image into an electrical signal. The image sensor is formed of a charge coupled device (CCD) image sensor or a complementary metal oxide semiconductor (CMOS) image sensor. In a case where the image sensor is formed of the CCD image sensor, for example, a signal processing unit (not illustrated) which performs signal processing (A/D conversion or the like) with respect to an electrical signal (analog signal) transmitted from the image sensor and outputs an imaging signal is mounted on a sensor chip or the like. In a case where the image sensor is formed of the CMOS image sensor, the imaging device includes, for example, a signal processing unit (not illustrated) which performs signal processing (A/D conversion or the like) with respect to an electrical signal (analog signal) which is converted from a light and outputs an imaging signal. The imaging unit 92 outputs a generated electrical signal to the communication module 93.

The communication module 93 outputs a signal transmitted from the control device 5 to the respective parts in the camera head 9 such as the camera head controller 94. The communication module 93 converts information relating to a current state of the camera head 9 or the like into a signal format corresponding to a predetermined transmission method, and outputs the converted signal to the control device 5 via the transmission cable 8. That is, the communication module 93 is a relay device that distributes the signals inputted from the control device 5 and the transmission cable 8 by serial-to-parallel conversion, for example, and outputs the signal to the respective portions of the camera head 9, and collectively outputs the signals from individual portion of the camera head 9 to be outputted to the control device 5 and the transmission cable 8 by parallel-to-serial conversion, for example.

The camera head controller 94 controls an entire operation of the camera head 9 in response to a drive signal inputted via the transmission cable 8, or an instruction signal outputted from an operating unit due to an operation of the operating unit such as a switch disposed on an outer surface of the camera head 9 in an exposed manner by a user. The camera head controller 94 outputs information relating to a current state of the camera head 9 to the control device 5 via the transmission cable 8.

The above-described communication module 93 and camera head controller 94 are realized by using a general-purpose processor such as a CPU having an internal memory (not illustrated) in which a program is stored, or a dedicated processor such as various calculation circuits which perform specific functions such as an ASIC. The above-described communication module 93 and camera head controller 94 may be realized by using an FPGA which is a kind of a programmable integrated circuit. In a case where the communication module 93 and the camera head controller 94 are realized by an FPGA, a memory for storing configuration data may be provided, and the FPGA which is a programmable integrated circuit may be configured based on configuration data read from the memory.

Further, the camera head 9 and the transmission cable 8 may be configured to include a signal processing unit which applies signal processing to an imaging signal generated by the communication module 93 or the imaging unit 92. An imaging clock for driving the imaging unit 92 and a control clock for controlling the camera head controller 94 may be generated based on a reference clock generated by an oscillator (not illustrated) disposed in the camera head 9, and the respective clocks may be outputted to the imaging unit 92 and the camera head controller 94 respectively. Alternatively, timing signals for various processing in the imaging unit 92 and the camera head controller 94 may be generated based on a synchronizing signal inputted from the control device 5 via the transmission cable 8, and the timing signals may be outputted to the imaging unit 92 and the camera head controller 94, respectively. The camera head controller 94 may be disposed on the transmission cable 8 or the control device 5 in place of the camera head 9.

The combination of the endoscope 2 and the camera head 9 mounted on the control device 5 is described with reference to FIG. 3A to FIG. 3D. FIG. 3A to FIG. 3D are schematic views illustrating the configuration of the endoscope 2 and the configuration of the camera head 9 according to the embodiment of the present invention. As the endoscope 2 and the camera head 9 mounted on the control device 5, endoscopes 2A, 2B and camera heads 9A, 9B as illustrated in FIG. 3A to FIG. 3D are provided. The endoscope 2A, 2B takes in an external light on a distal end side of the endoscope 2A, 2B, and the endoscope 2A, 2B is connected to the camera head 9 (9A, 9B) on a proximal end side of the endoscope 2A, 2B.

Figure 3A:
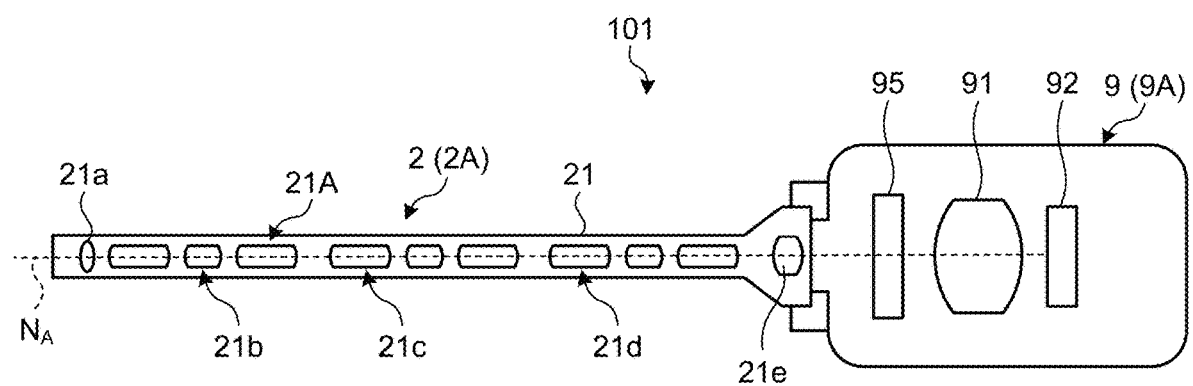
FIG. 3A is a schematic view for explaining the configuration of an endoscope and the configuration of the camera head according to the first embodiment of the present invention.

The endoscope 2A includes an observation optical system 21A in an insertion portion 21 (for example, see FIG. 3A). In the observation optical system 21A, an objective lens 21a, a first relay optical system 21b, a second relay optical system 21c, a third relay optical system 21d, and an eyepiece 21e are arranged in this order from a distal end side of the observation optical system 21A along an optical axis NA of the observation optical system 21A.

Figure 3B:
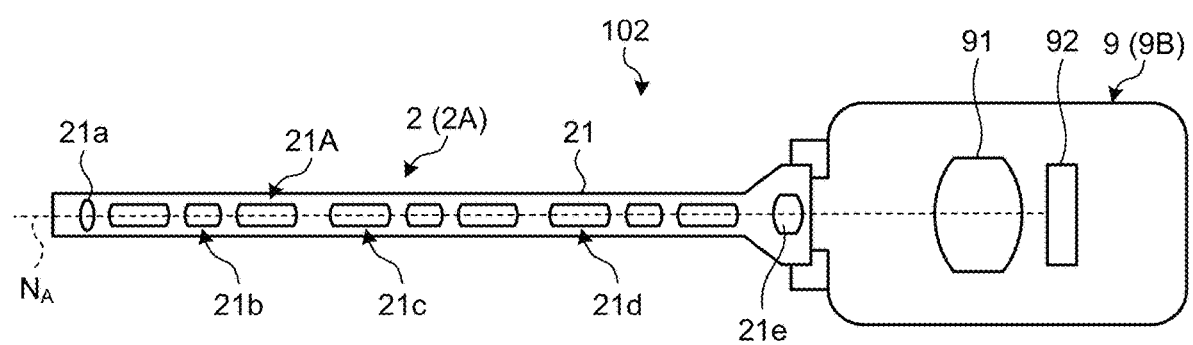
FIG. 3B is a schematic view for explaining the configuration of the endoscope and the configuration of the camera head according to the first embodiment of the present invention.
Figure 3C:
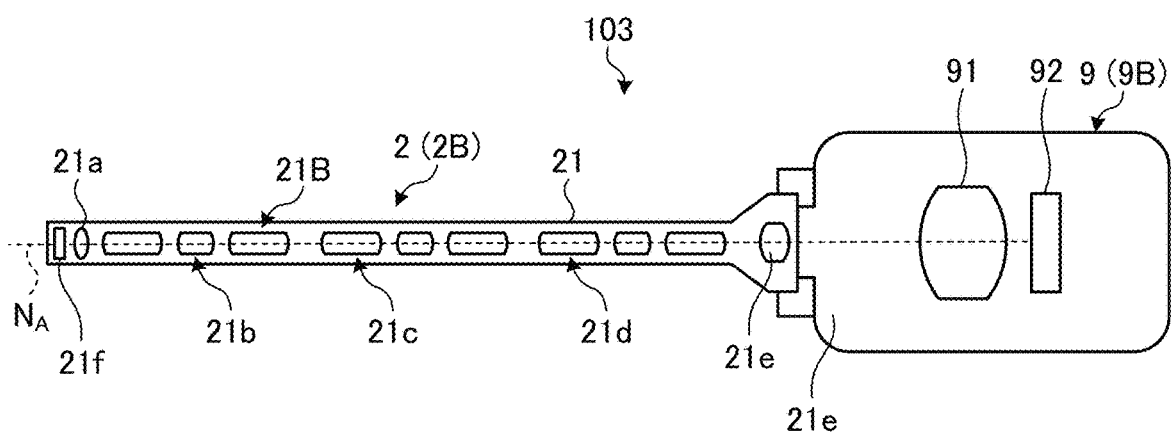
FIG. 3C is a schematic view for explaining the configuration of the endoscope and the configuration of the camera head according to the first embodiment of the present invention.
Figure 3D:
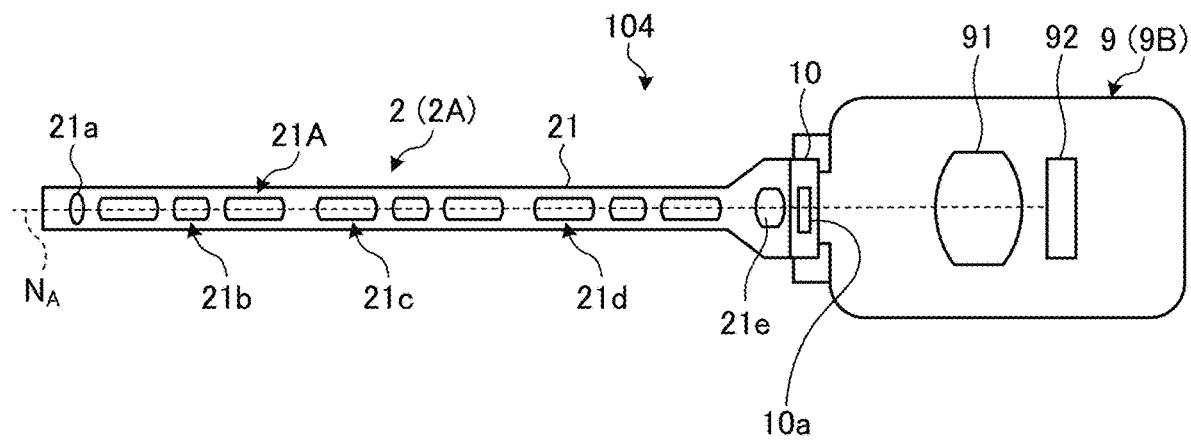
FIG. 3D is a schematic view for explaining the configuration of the endoscope and the configuration of the camera head according to the first embodiment of the present invention.

The endoscope 2B includes an observation optical system 21B in the insertion portion 21 (for example, see FIG. 3C). In the observation optical system 21B, an observation-side filter 21f, an objective lens 21a, a first relay optical system 21b, a second relay optical system 21c, a third relay optical system 21d, and an eyepiece 21e are arranged in this order from a distal end side of the observation optical system 21B along an optical axis NB of the observation optical system 21B. The endoscope 2B is formed by adding the observation-side filter 21f which cuts a light in a predetermined wavelength band to the configuration of the endoscope 2A. The observation-side filter 21f may be replaced by a configuration where coating is applied to any one of the optical members which form the observation optical system 21B for cutting a light in a predetermined wavelength band.

In the camera head 9A, an observation-side filter 95, a lens unit 91, and an imaging unit 92 are arranged in this order from a side where the camera head 9 is connected to the endoscope 2 (for example, see FIG. 3A).

In the camera head 9B, a lens unit 91 and an imaging unit 92 are arranged in this order from a side where the camera head 9B is connected to the endoscope 2 (for example, see FIG. 3B). The camera head 9B is formed by removing the observation-side filter 95 which cuts a light in a predetermined wavelength band from the configuration of the camera head 9A.

In the first embodiment, an image acquisition device is formed by combining the endoscope 2 and the camera head 9 to each other (transmission cable 8 not illustrated in FIG. 3A to FIG. 3D). For example, an image acquisition device 101 is formed of the endoscope 2A and the camera head 9A (see FIG. 3A), an image acquisition device 102 is formed of the endoscope 2A and the camera head 9B (see FIG. 3B), and an image acquisition device 103 is formed of the endoscope 2B and the camera head 9B (see FIG. 3C). The configurations illustrated in FIG. 3A to FIG. 3C include the configuration where the endoscope 2 and the camera head 9 are detachably connected to each other, and the configuration where the endoscope 2 and the camera head 9 are fixed to each other (integrally formed with each other). Besides the configurations illustrated in FIG. 3A to FIG. 3C, it is also possible to use an image acquisition device 104 formed by arranging an intermediate member 10 having an observation-side filter 10a between the endoscope 2A and the camera head 9B (See FIG. 3D). The intermediate member 10 may be detachably connected to the endoscope 2A and the camera head 9B, or the observation-side filter 10a may be insertable into and removable from the intermediate member 10. In the first embodiment, any one of the above-described image acquisition devices 101 to 104 is selectively connected to the control device 5.

In the first embodiment, due to the combination of the endoscope 2 and the camera head 9, it is possible to provide the configuration having one observation-side filter (observation-side filter 10a, 21f, 95) or the configuration having no observation-side filter (observation-side filter 10a, 21f, 95). The configuration may be formed so as to have two observation-side filters (observation-side filters 21f, 95) as in the case of the combination of the endoscope 2B and the camera head 9A. However, it is sufficient for the medical observation system to have one observation-side filter and hence, in this embodiment, the description is made by taking two patterns, that is, the pattern where the medical observation system has one observation-side filter, and the pattern where the medical observation system has no observation-side filter.

FIG. 4 is a view for explaining the sensitivity of the observation-side filter provided during the special light observation in the endoscope device according to the first embodiment. During the normal observation, when the observation-side filter is not provided on the observation optical path, all lights which form a white light are incident on the imaging unit 92 (see (a) in FIG. 4). That is, in the normal observation, the endoscope device is formed to have the sensitivity with respect to all lights. The white light according to the first embodiment includes a light in a blue wavelength band (B light), a light in a green wavelength band (G light), a light in a red wavelength band (R light), a light in a near infrared wavelength band (hereinafter, also referred to as a near-infrared excitation light), and a fluorescence (a fluorescent self-luminous light) applied by coating to a surface of the light source. In FIG. 4, a wavelength of a light becomes larger toward a right side. A wavelength band of a light used for a near-infrared excitation light is 700 nm to 800 nm, for example. A wavelength of a fluorescence is larger than a wavelength of the used near-infrared light, and includes a fluorescence of indocyanine green and a fluorescence derived from a light source.

To the contrary, during the special light observation, a near-infrared excitation light is emitted from the light source device 6, and the observation-side filter (any of the observation-side filters 10a, 21f, and 95) is disposed on the observation optical path. The observation-side filter has low sensitivity with respect to a light in a near-infrared wavelength band emitted from the light source device 6 as an illumination light (see (b) in FIG. 4). Accordingly, in a case where the observation-side filter is disposed, a light which the imaging unit 92 receives becomes lights in a wavelength band excluding the near infrared wavelength band.

Figure 5:
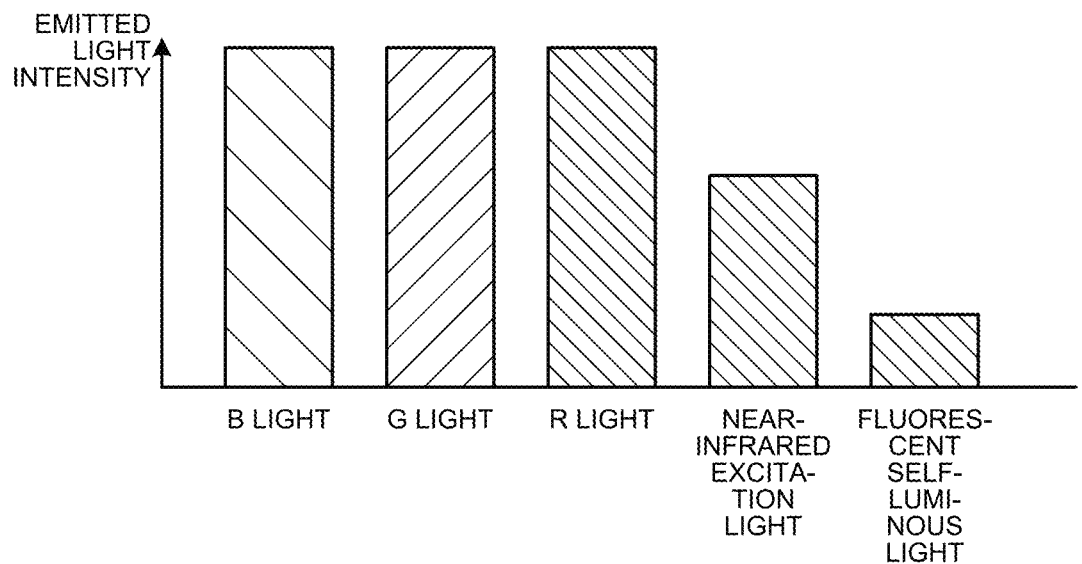
FIG. 5 is a view for explaining a light which a light source of a light source device emits in the endoscope device according to the first embodiment.

Next, an illumination light emitted by the light source device 6 is described with reference to FIG. 5 to FIG. 7. FIG. 5 is a view for explaining lights which the light source of the light source device emits in the endoscope device according to the first embodiment. FIG. 5 illustrates intensities of lights when the light source which the light source device 6 includes is a halogen lamp. A fluorescent self-luminous light which an illumination light emitted by the halogen lamp includes is fluorescence derived from a fluorescent paint applied by coating to a surface of the halogen lamp. The description is made hereinafter assuming that, in the graph, a wavelength is increased toward a right side on an axis of abscissa of a graph.

Figure 6:
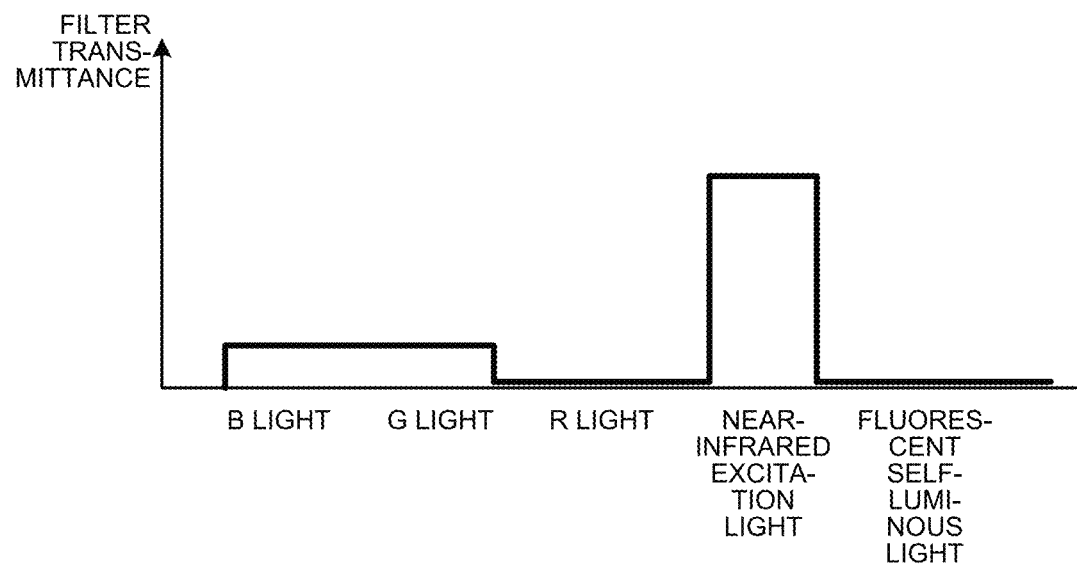
FIG. 6 is a view for explaining light transmittance of a light-source-side filter provided during the special light observation in the endoscope device according to the first embodiment.

FIG. 6 is a view for explaining light transmittance of a light-source-side filter provided during the special light observation in the endoscope device according to the first embodiment. During the special light observation, the illumination-side filter is disposed on an illumination optical path in the light source device 6 under the control of the control unit 56. In the illumination-side filter, the filter transmittance of the B light, the filter transmittance of the G light, the filter transmittance of the R light and the filter transmittance of the fluorescent self-luminous light are smaller than the filter transmittance of the near-infrared excitation light. Further, the filter transmittance of the R light and the filter transmittance of the fluorescent self-luminous light are smaller than the filter transmittance of the B light and the filter transmittance of the G light. In the description made hereinafter, the description is made assuming that the R light and the fluorescent self-luminous light are substantially cut by the illumination-side filter. The illumination-side filter may be disposed outside the light source device 6, for example, at an end portion of the light guide or in the endoscope 2.

Figure 7:
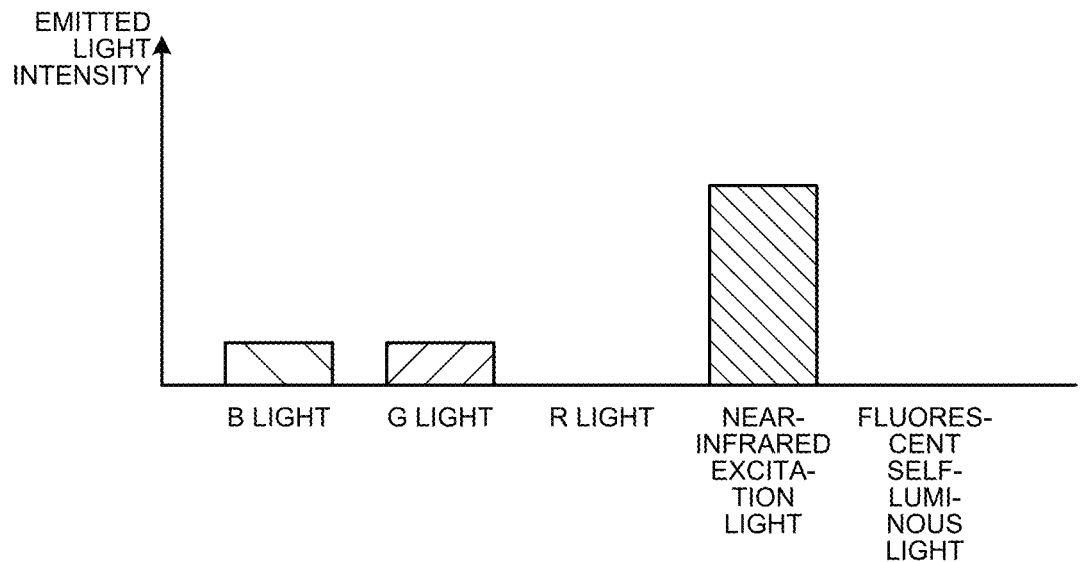
FIG. 7 is a view for explaining a light emitted during the special light observation in the endoscope device according to the first embodiment.

FIG. 7 is a view for explaining a light emitted during the special light observation in the endoscope device according to the first embodiment. A Light is emitted from the light source illustrated in FIG. 5, and the light which has passed the illumination-side filter illustrated in FIG. 6 includes a B light, a G light, and a near-infrared excitation light as illustrated in FIG. 7. A subject is irradiated with the special light which includes the B light, the G light, and the near-infrared excitation light. When the subject is irradiated with the special light (near-infrared excitation light), the indocyanine green of the subject is excited and emits fluorescence. At this stage of the operation, the fluorescent self-luminous light exhibits small sensitivity to the image sensor. Accordingly, to make the fluorescent self-luminous light emit light strongly, it is desirable to make near-infrared excitation light more strongly than the B light and the G light.

Figure 8:
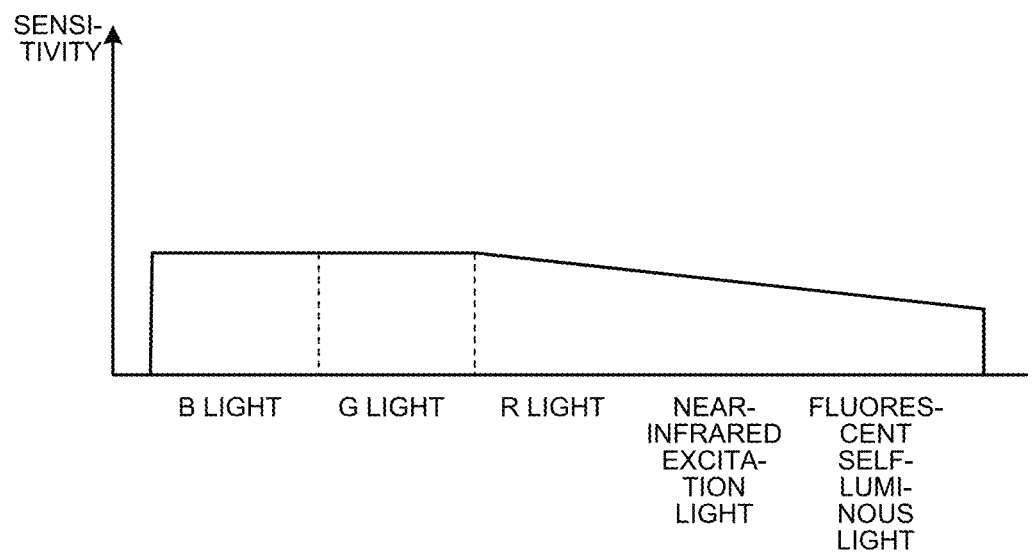
FIG. 8 is a view for explaining sensitivity of an image sensor which the endoscope device according to the first embodiment includes.

Next, the sensitivity of the imaging unit 92 is described with reference to FIG. 8. FIG. 8 is a view for explaining the sensitivity of an image sensor which the endoscope device according to the first embodiment includes. The image sensor which the imaging unit 92 includes has the sensitivity with respect to the B light, the G light, the R light, the near-infrared excitation light, and the fluorescent self-luminous light, respectively. In this image sensor, with respect to the R light, the near-infrared excitation light, and the fluorescent self-luminous light, sensitivity is decreased as a wavelength is increased. In the image sensor, the near-infrared excitation light and the fluorescent self-luminous light are received by pixels which receive the R light.

Figure 9:
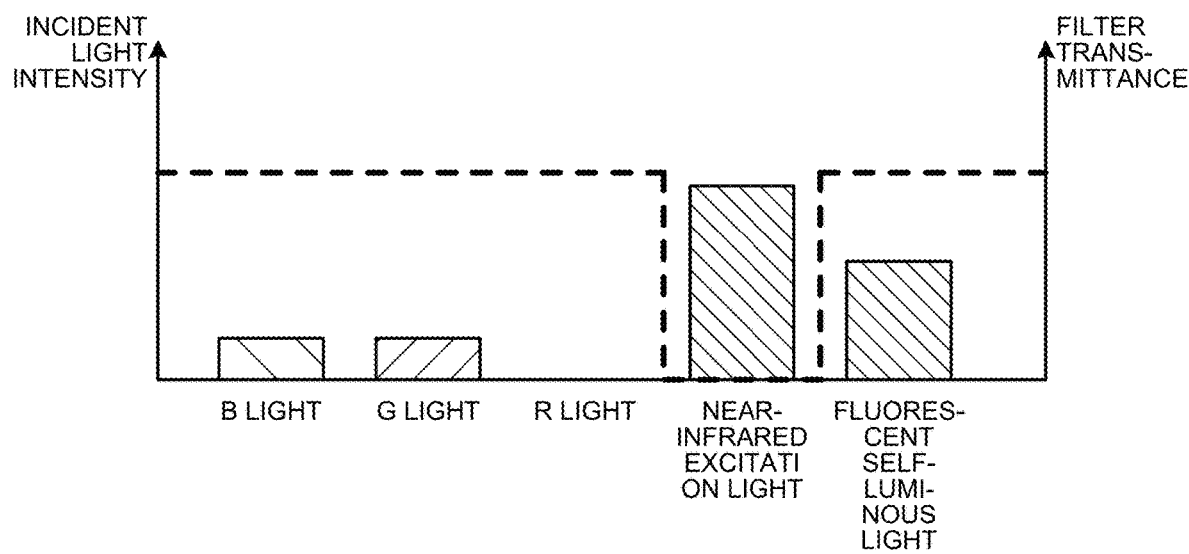
FIG. 9 is a view for explaining a light which is incident on the endoscope during the special light observation in the endoscope device according to the first embodiment.
Figure 10:
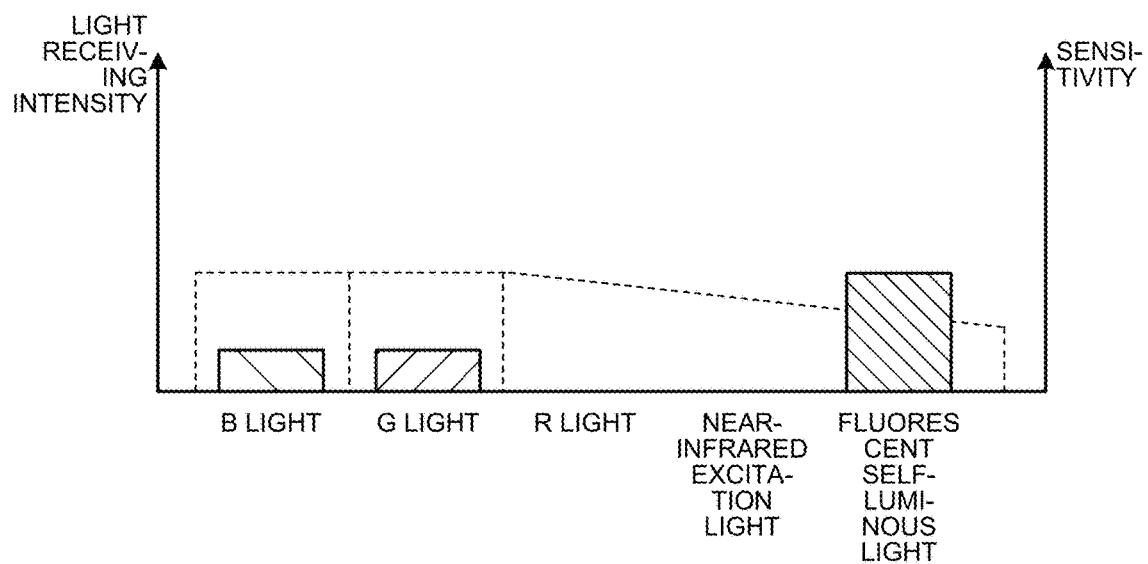
FIG. 10 is a view for explaining a light which is incident on the image sensor during the special light observation in the endoscope device according to the first embodiment.

FIG. 9 and FIG. 10 are views for explaining a light which is incident on the endoscope during the special light observation in the endoscope device according to the first embodiment. FIG. 9 and FIG. 10 indicate the intensities of the respective lights (the B light, the G light, the R light, the near-infrared excitation light, and the fluorescent self-luminous light). A broken line in FIG. 9 indicates the transmittance of the observation-side filter (see (b) in FIG. 4). A broken line in FIG. 10 indicates the sensitivity of the imaging unit 92 (see FIG. 8).

During the special light observation, an observation light which is incident on the endoscope 2 is emitted from the light source device 6, and includes the B light, the G light and the near-infrared excitation light which are reflected by the subject, and the fluorescent self-luminous light which the indocyanine green emits. With respect to this observation light, the near-infrared excitation light is cut by the observation-side filter. That is, the imaging unit 92 receives the B light, the G light, and the fluorescent self-luminous light (see FIG. 10).

To the contrary, during the normal observation, an illumination light which includes the B light, the G light, the R light, the near-infrared excitation light, and the fluorescent self-luminous light is irradiated to the subject, and the lights reflected on the subject are incident on the imaging unit 92.

Figure 11:
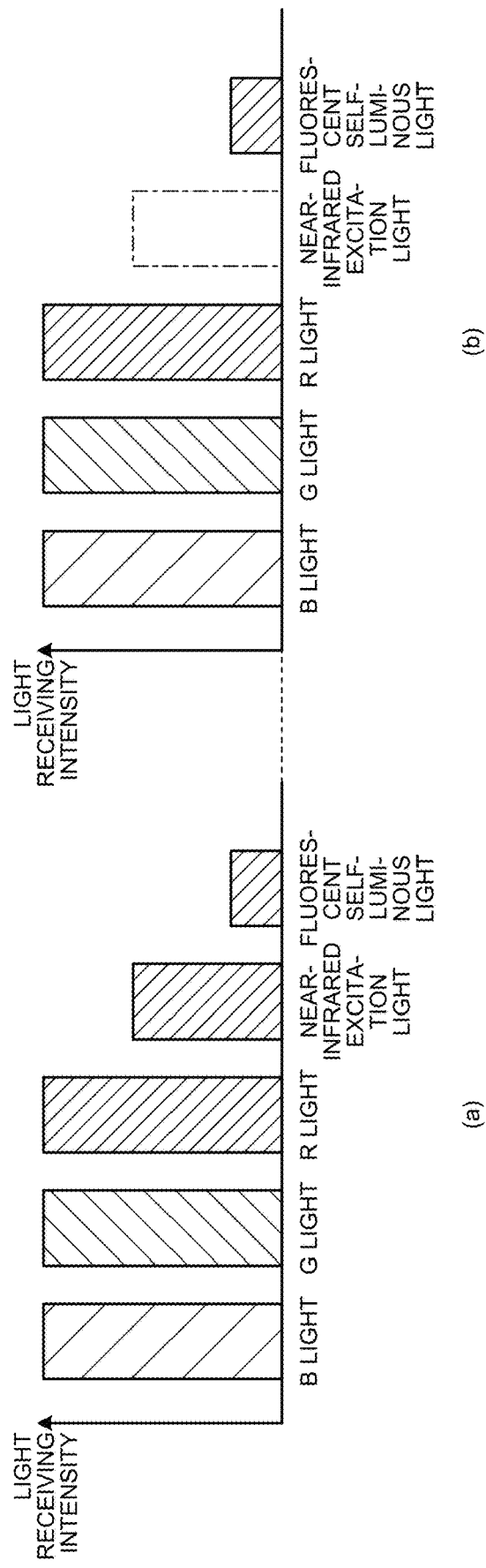
FIG. 11 is a view for explaining the difference in an incident light on an image sensor depending on the presence or absence of the observation-side filter in the endoscope device according to the first embodiment.

FIG. 11 is a view for explaining the difference in the incident light on the image sensor depending on the presence or absence of the observation-side filter in the endoscope device according to the first embodiment. As described above, in the normal observation, the observation-side filter is not provided. Accordingly, when the reflected light of the illumination light is received, the reflected light includes the B light, the G light, the R light, the near-infrared excitation light, and the fluorescent self-luminous light (see (a) of FIG. 11). To the contrary, in the special light observation, the illumination light filter and the observation-side filter are provided. Accordingly, when the reflected light of the illumination light is received, the reflected light becomes a light which includes the B light, the G light, the R light, and the fluorescent self-luminous light (see (b) of FIG. 11).

Figure 12:
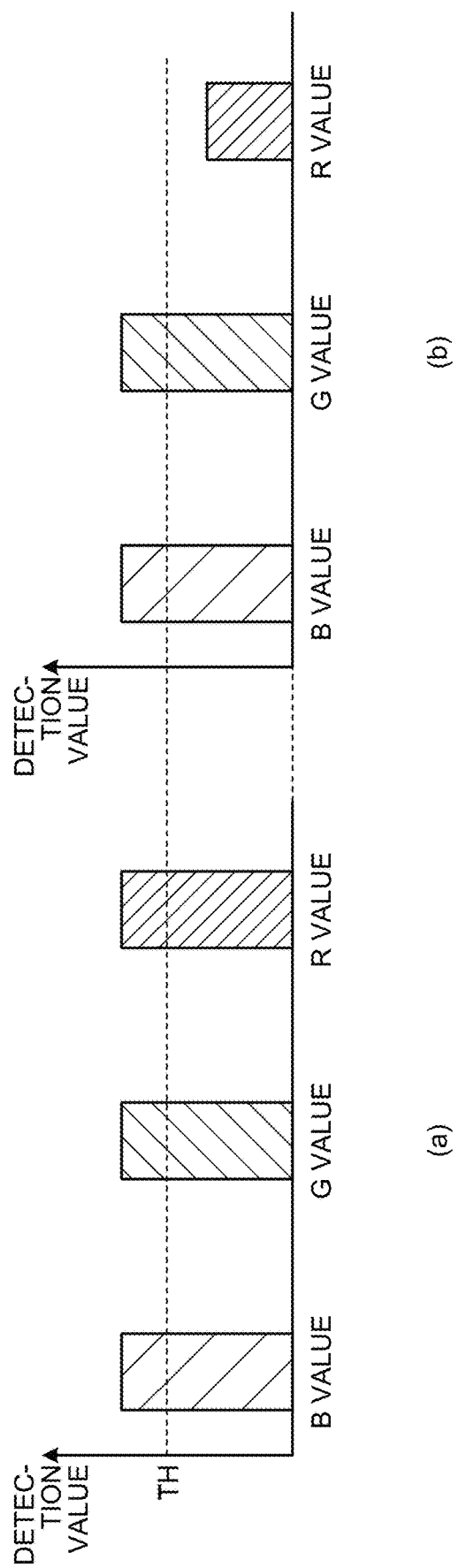
FIG. 12 is a view for explaining a detection wave value by the incident light illustrated in FIG. 11.

FIG. 12 is a view for explaining detection values by the incident light illustrated in FIG. 11. In the detection processing, the near-infrared excitation light and the fluorescent self-luminous light are processed as the R light. At this stage of the operation, to compare the detection values in a case where the observation-side filter is inserted in the optical path (see (b) in FIG. 12) with the detection values in a case where the observation-side filter is not inserted in the optical path (see (a) in FIG. 12), the R light (R value) is lowered. This is because the near-infrared excitation light is cut by the observation-side filter. There is no large difference between the normal observation and the special light observation with respect to the detection value of the B light (B value) and the detection value of the G light (G value).

The filter detection unit 52a determines whether or not the observation-side filter exists on the observation optical path by making use of the difference in the detection value (R value) depending on the presence or absence of the observation-side filter. Specifically, in the filter detection unit 52a, a threshold value is set with respect to the detection value (in this embodiment, the R value), and the filter detection unit 52a determines whether or not the obtained detection value is equal to or more than the threshold value TH. This threshold value TH is set based on, for example, at least one of a wavelength (wavelength band) of a light emitted from the light source, the sensitivity of the image sensor, the spectral characteristic (attenuation rate) of the lens, and a change rate of the detection value depending on the presence or absence of the observation-side filter. When the R value is equal to or more than the threshold value TH, the filter detection unit 52a determines that the observation-side filter does not exist on the observation optical path. On the other hand, when the R value is less than the threshold value TH, the filter detection unit 52a determines that the observation-side filter exists on the observation optical path.

The above-mentioned filter detection processing is performed, for example, at the time of calibration where the white balance adjustment processing is performed. Specifically, before the use of the endoscope 2 is started, when a calibration instruction is inputted from a user via a button or the like mounted on the input unit 54 or the camera head 9, the control unit 56 performs the calibration processing (for example, the white balance adjustment processing) and, at the same time, and performs the filter detection processing. The filter detection processing is performed not only during the above-described white balance adjustment processing but also when an instruction is given from a user via the buttons or the like mounted on the input unit 54 or the camera head 9.

When the control unit 56 acquires the detection result from the filter detection unit 52a, the control unit 56 performs the setting of a color mode, the notification processing, and the emission control of an illumination light.

In the setting processing of a color mode, when it is determined that the observation-side filter does not exist on the observation optical path, the control unit 56 sets the color mode to a normal white light image. In the color mode of the normal white light image, the color correction is performed for reproducing an appropriate white color. On the other hand, when it is determined that the observation-side filter exists on the observation optical path, the control unit 56 sets the color mode corresponding to an image which does not include the near-infrared excitation light. In the color mode of the image which does not include the near-infrared excitation light, the color correction is performed where a gain value of red (R) is increased. When the control unit 56 determines that the observation-side filter exists on the observation optical path, the control unit 56 may perform a control of allowing the setting to a mode during the fluorescence observation.

In the notification processing, for example, in a case where the filter detection unit 52a determines that the observation-side filter does not exist on the observation optical path, the filter detection unit 52a performs the notification indicating that the observation-side filter does not exist when the instruction to perform the special light observation is inputted via the input unit 54. For example, as illustrated in FIG. 3B, in a case where the observation-side filter is not provided to either the endoscope 2 (2A) or the camera head 9 (9B), when an instruction to perform the special light observation is inputted via the input unit 54, the notification indicating that the observation-side filter does not exist is performed. The notification processing at this stage of operation is performed by textual information (an image) which the display device 4 displays, a sound or a light which the output unit 55 outputs or the like.

In a case where it is determined that the observation-side filter does not exist on the observation optical path, the emission of the special light from the light source device 6 is stopped when the instruction to perform the special light observation is inputted via the input unit 54. When the presence of the observation-side filter on the observation optical path is detected, the control unit 56 releases the stopping of emission of the special light. The light source controller 62 controls an emission of light from the light source unit 61 under the control of the control unit 56.

The control unit 56 performs at least one of the above-described notification processing and the illumination light control corresponding to the detection result of the filter detection unit 52a.

In the first embodiment described above, it is possible to detect the presence or absence of the observation-side filter using the detection value without additionally providing a detection block. According to the first embodiment, it is possible to detect the presence or absence of a filter in the observation optical system while suppressing the increase of the scale of a circuit. As a result, it is possible to prevent the erroneous observation due to the presence or absence of the filter.

Particularly, it is possible to prevent the special light observation from being performed in a state where the observation-side filter does not exist on the observation optical path. Further, according to the above-described first embodiment, it is possible to perform the observation in the observation mode (color mode) in accordance with a kind of the endoscope 2.

First Modification of First Embodiment

Subsequently, a first modification of the first embodiment of the present invention is described. An endoscope device according to the first modification differs from the above-described endoscope device 1 only with respect to a light source which a light source device 6 includes, and the other configurations are equal to the corresponding configurations of the above-described endoscope device 1. Hereinafter, the description is made with respect to portions which make the first modification different from the above-described first embodiment. In the first modification, the light source device 6 includes, as a light source, an LED (Light Emitting Diode) which emits a white light, and a semiconductor laser which emits a light in a near-infrared wavelength band. Under the control of a control unit 56, the LED light source emits a light during the normal observation, and the semiconductor laser emits a light during the special light observation.

Figure 13:
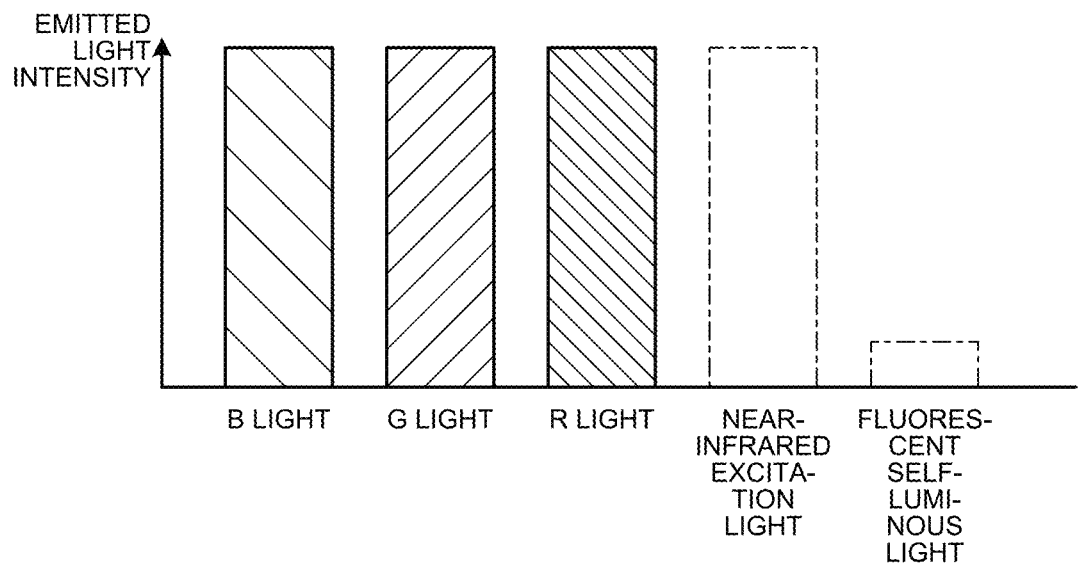
FIG. 13 is a view for explaining a light which a light source of a light source device emits during normal observation in an endoscope device according to a modification of the first embodiment.

FIG. 13 is a view for explaining a light which a light source of a light source device emits during normal observation in the endoscope device according to the first modification. FIG. 13 illustrates the intensity of a light in a case where the light source is an LED. In FIG. 13, wavelengths of lights become larger toward a right side. As illustrated in FIG. 13, the light emitted from the LED light source includes the light in a blue wavelength band (the B light), the light in a green wavelength band (the G light) and the light in a red wavelength band (the R light). In the case where the light source is the LED, a near-infrared excitation light and a fluorescent self-luminous light are not emitted. Accordingly, the light emission is switched to the light emission by the semiconductor laser during special light observation.

Figure 14:
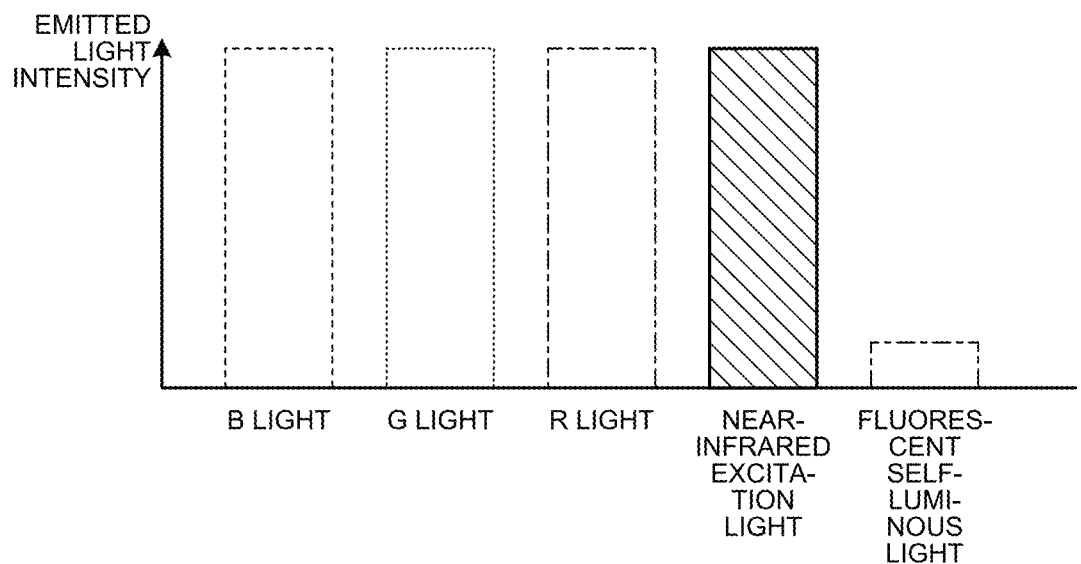
FIG. 14 is a view for explaining a light which the light source of the light source device emits during the special light observation in the endoscope device according to the modification of the first embodiment.

FIG. 14 is a view for explaining a light which the light source of the light source device emits during the special light observation in the endoscope device according to the first modification. FIG. 14 illustrates the intensity of light of the semiconductor laser which emits a light in a near infrared wavelength band. As illustrated in FIG. 14, the light emitted from the semiconductor laser is formed of a near-infrared excitation light. A fluorescent self-luminous light illustrated in FIG. 13 and FIG. 14 indicates fluorescence which indocyanine green emits.

Figure 15:
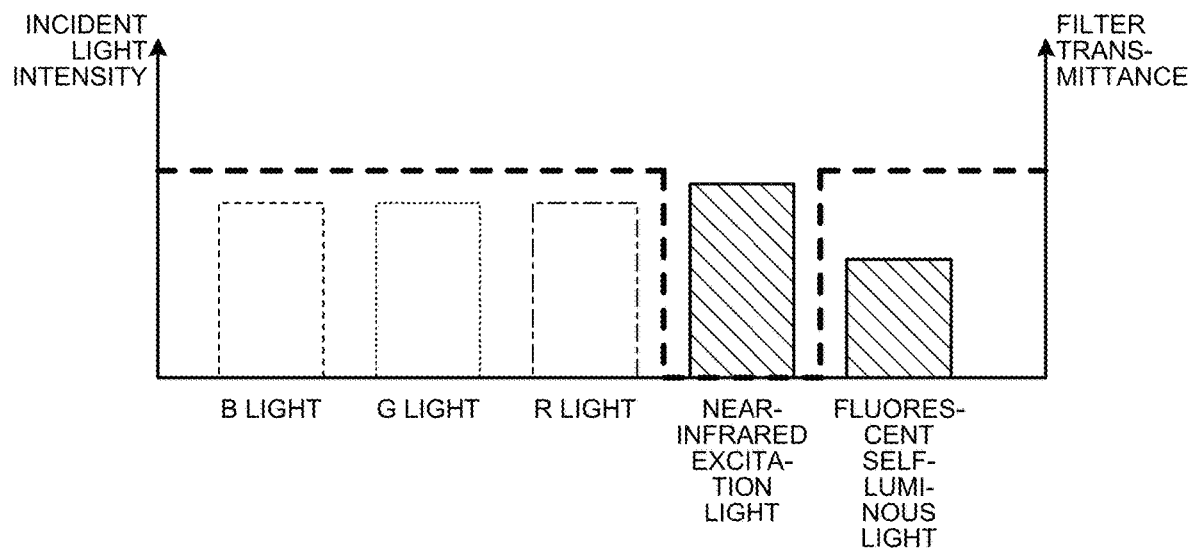
FIG. 15 is a view for explaining a light which is incident on an endoscope during the special light observation in the endoscope device according to the modification of the first embodiment.
Figure 16:
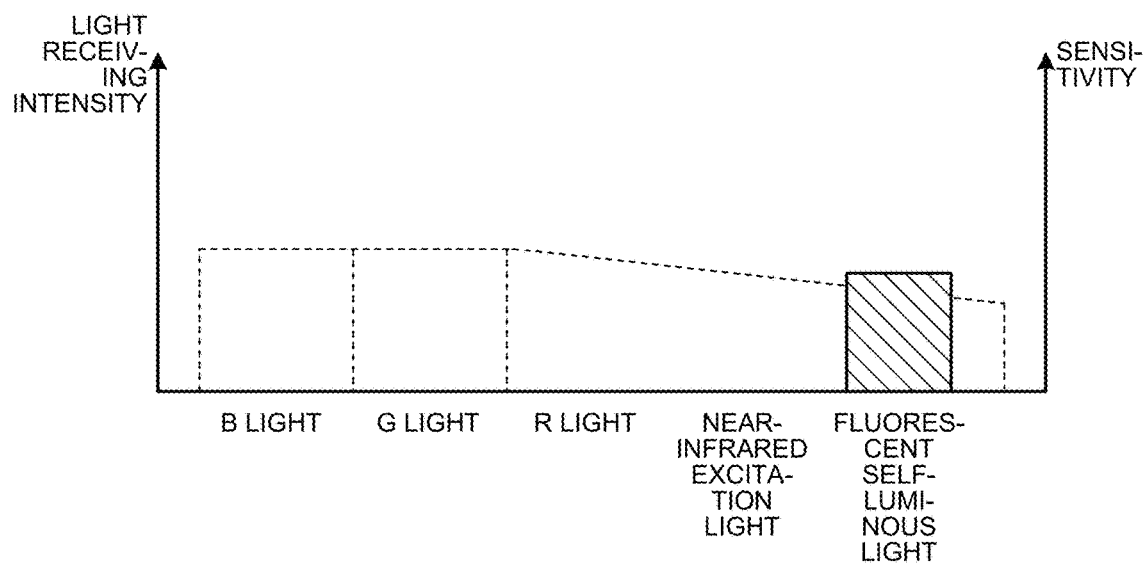
FIG. 16 is a view for explaining a light which is incident on an image sensor during the special light observation in the endoscope device according to the modification of the first embodiment.

FIG. 15 and FIG. 16 are views for explaining lights which are incident on an endoscope during the special light observation in the endoscope device according to the first modification of the first embodiment. FIG. 15 and FIG. 16 illustrate the intensities of the respective lights (the B light, the G light, the R light, the near-infrared excitation light, and the fluorescent self-luminous light). A broken line in FIG. 15 illustrates the transmittance of an observation-side filter (see (b) in FIG. 4). A broken line in FIG. 16 indicates the sensitivity of an imaging unit 92 (see FIG. 8).

In this first modification, during the special light observation, an observation light which is incident on the endoscope 2 is emitted from the light source device 6, and is formed of the near-infrared excitation light reflected by a subject, and the fluorescent self-luminous light which the indocyanine green emits (see FIG. 15). With respect to this observation light, the near-infrared excitation light is cut by the observation-side filter. That is, the imaging unit 92 receives only the fluorescence emitted by the indocyanine green (see FIG. 16).

To the contrary, during the normal observation, an illumination light including the B light, the G light, and the R light is irradiated to a subject, and the light reflected by the subject is incident on the imaging unit 92.

Figure 17:
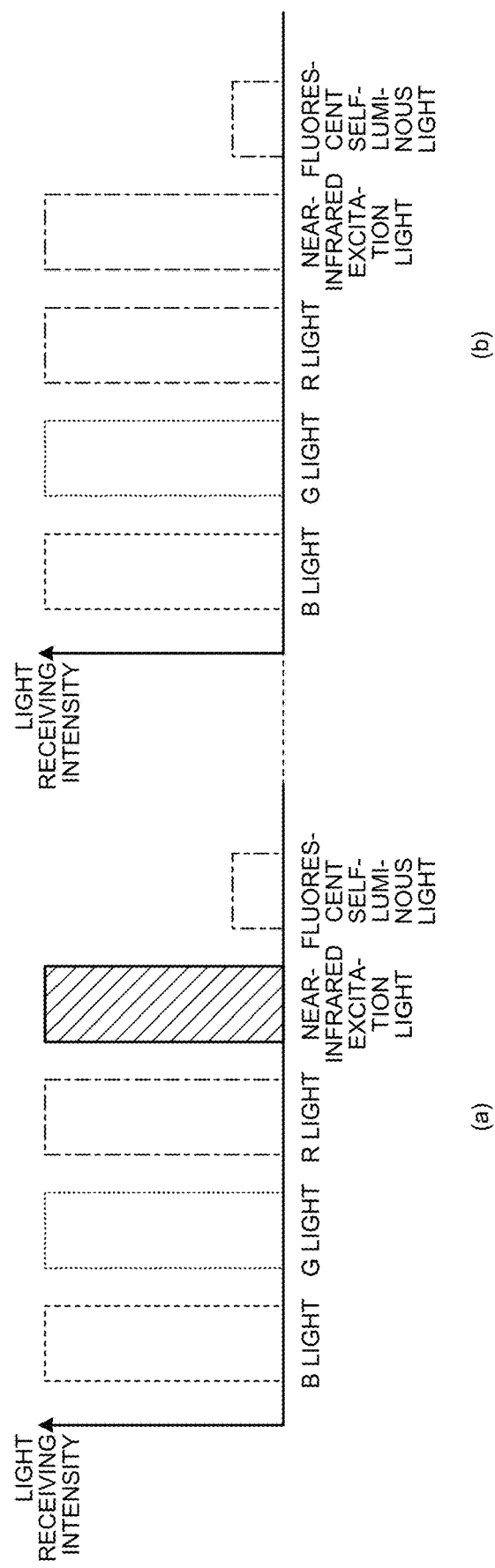
FIG. 17 is a view for explaining the difference in incident light on the image sensor depending on the presence or absence of an observation-side filter in the endoscope device according to the modification of the first embodiment.

FIG. 17 is a view for explaining the difference in incident light on an image sensor depending on the presence or absence of an observation-side filter in the endoscope device according to the first modification of the first embodiment. In a case where the semiconductor laser is used as the light source and the observation-side filter is not provided on the observation optical path, a light which the imaging unit 92 receives is formed of only the near-infrared excitation light (see (a) of FIG. 17). On the other hand, in a case where the observation-side filter is provided on the observation optical path, even when the near-infrared excitation light is emitted, the reflected light of the near-infrared excitation light is cut and hence, there is no possibility that the imaging unit 92 receives the reflected light (the near-infrared excitation light) (see (b) of FIG. 17).

Figure 18:
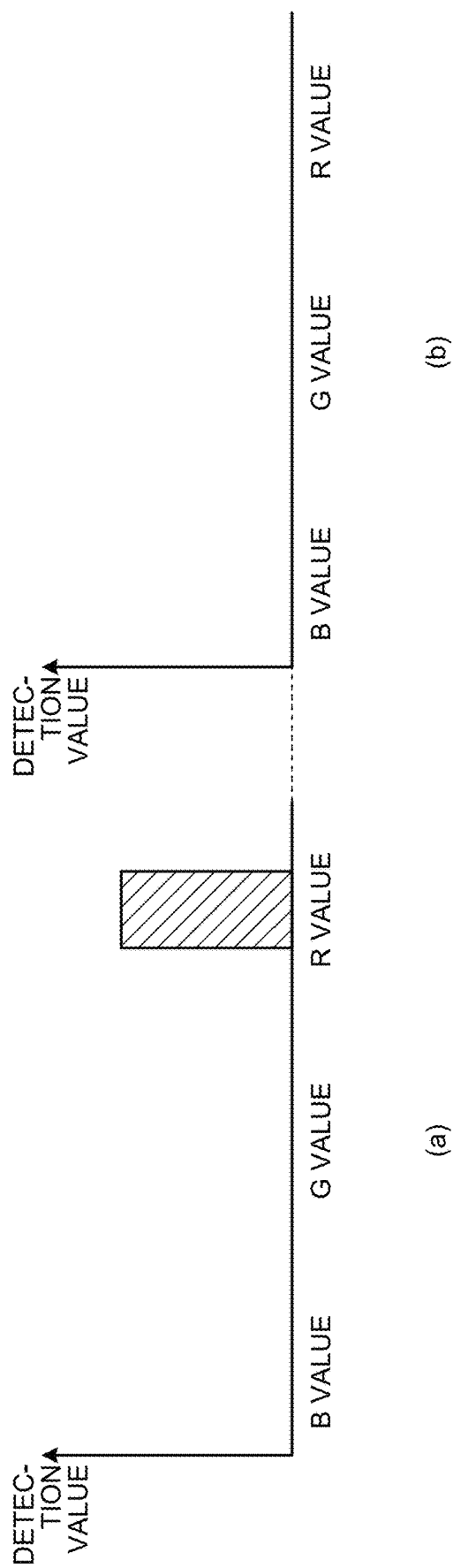
FIG. 18 is a view for explaining a detection wave value by the incident light illustrated in FIG. 17.

FIG. 18 is a view for explaining a detection value based on the incident light illustrated in FIG. 17. In the detection processing, the near-infrared excitation light is processed as the R light and hence, an R value in a case where the observation-side filter is not inserted in the optical path becomes a value corresponding to the reflected light of the near-infrared excitation light (see (a) of FIG. 18). On the other hand, an R value in a case where the observation-side filter is inserted in the optical path becomes zero (see (b) in FIG. 18). The filter detection processing is performed during the white balance adjustment processing or after the white balance adjustment processing, for example.

In the same manner as the first embodiment, the filter detection unit 52*a* determines whether or not the observation-side filter exists on the observation optical path by using the difference in detection value depending on the presence or absence of the observation-side filter. Specifically, the filter detection unit 52*a* determines whether or not the R value may be obtained. When the R value is obtained, the filter detection unit 52*a* determines that the observation-side filter does not exist on the observation optical path. On the other hand, in a case where the detection value is not obtained, the filter detection unit 52*a* determines that the observation-side filter exists on the observation optical path.

When the control unit 56 acquires the detection result from the filter detection unit 52*a*, the control unit 56 performs at least one of the above-described notification processing, the illumination light control, and the color mode setting control corresponding to the detection result of the filter detection unit 52*a*.

In the first modification described above, it is possible to detect the presence or absence of the observation-side filter by using the detection value without additionally providing a detection block. According to the first modification, it is possible to detect the presence or absence of a filter in the observation optical system while suppressing an increase of the scale of a circuit.

Second Modification of First Embodiment

Figure 19:
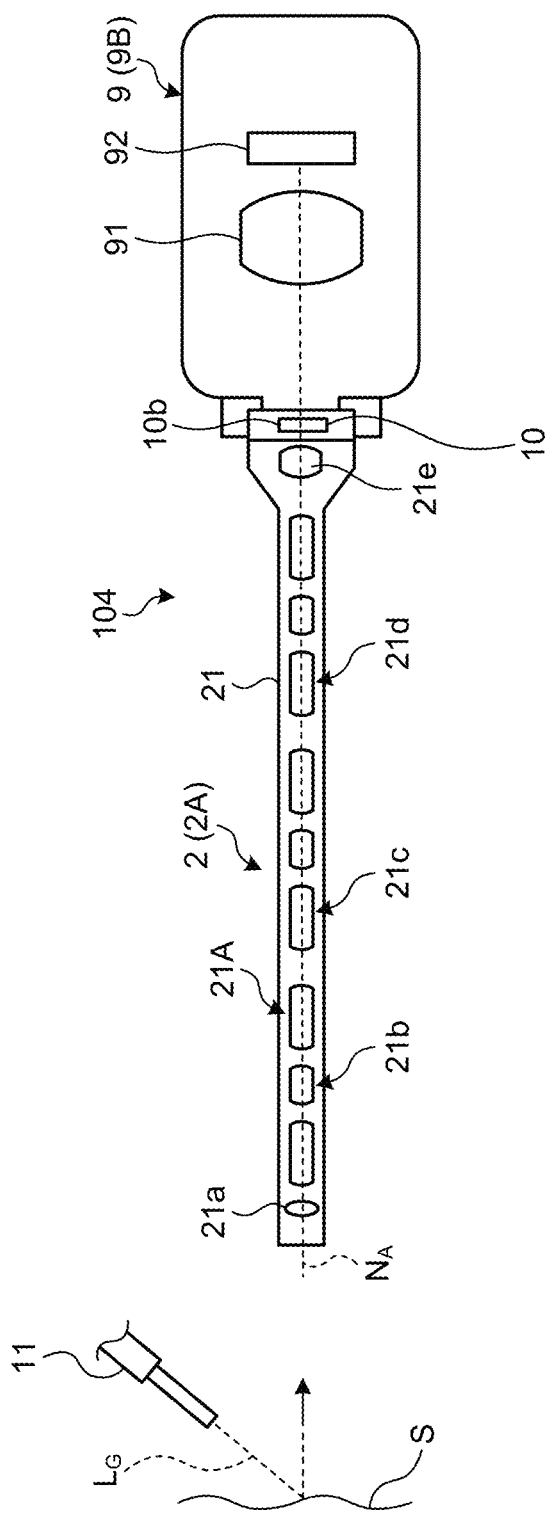
FIG. 19 is a schematic view for explaining configuration of an endoscope 2 and the configuration of a camera head 9 according to a second modification of the first embodiment of the present invention.

Subsequently, a second modification of the first embodiment of the present invention is described. An endoscope device according to the second modification is equal to the endoscope device 1 described above. Hereinafter, the description is made with respect to portions which make the first modification different from the above-described first embodiment. FIG. 19 is a schematic view for explaining the configuration of an endoscope 2 and the configuration of a camera head 9 according to the second modification of the first embodiment of the present invention. In the second modification, the description is made by taking the combination of an endoscope 2A, a camera head 9B, and an intermediate member 10A (see the image acquisition device 104 in FIG. 3D) as an example. In the second modification, a treatment is applied to an object S using a laser treatment tool 11 by irradiating a laser light $L_G$ having a predetermined wavelength (or wavelength band) included in a green wavelength band to the object S. At this stage of the operation, a change in brightness of an image due to a laser light $L_G$ is suppressed by cutting a light of a wavelength (or a wavelength band) of the laser light $L_G$ using an observation-side filter.

The intermediate member 10A has an observation-side filter 10b which cuts a light in a wavelength band of the laser light $L_G$.

In the control device 5, the filter detection unit 52a detects whether or not the observation-side filter (here, the observation-side filter 10b) is disposed in the observation optical system in the same manner as the case of the R value of the first embodiment. In the same manner as the first embodiment, the filter detection unit 52a detects the presence or absence of the observation-side filter 10b in the observation optical system by using the difference in detection value (G value) of a G light depending on the presence or absence of the observation-side filter 10b.

The control unit 56 performs notification processing or an illumination light control based on a detection result of the observation-side filter. In the second modification, when it is detected that the observation-side filter is not disposed, a message indicating that the observation-side filter should be mounted in using the laser treatment tool 11 is displayed, or a notification that the observation-side filter should be mounted is performed by generating a sound and/or emitting a light. Further, provided that the control unit 56 may control the light emission of the laser treatment tool 11, the control unit 56 may prohibit the light emission of the laser treatment tool 11 when it is detected that the observation-side filter is not disposed.

In the second modification, by detecting the presence or absence of the observation-side filter 10b and by urging an operator to mount the observation-side filter 10b in using the laser treatment tool, a change in brightness of a display image by the laser light $L_G$ may be suppressed. The intensity of a laser light used for the treatment of a subject is larger than the intensity of the illumination light which a light source device 6 emits and hence, there is a concern that, when an imaging unit 92 receives the laser light, an observation image may not be properly obtained. By providing the observation-side filter, an image suitable for observation may be generated.

Second Embodiment

Figure 20:
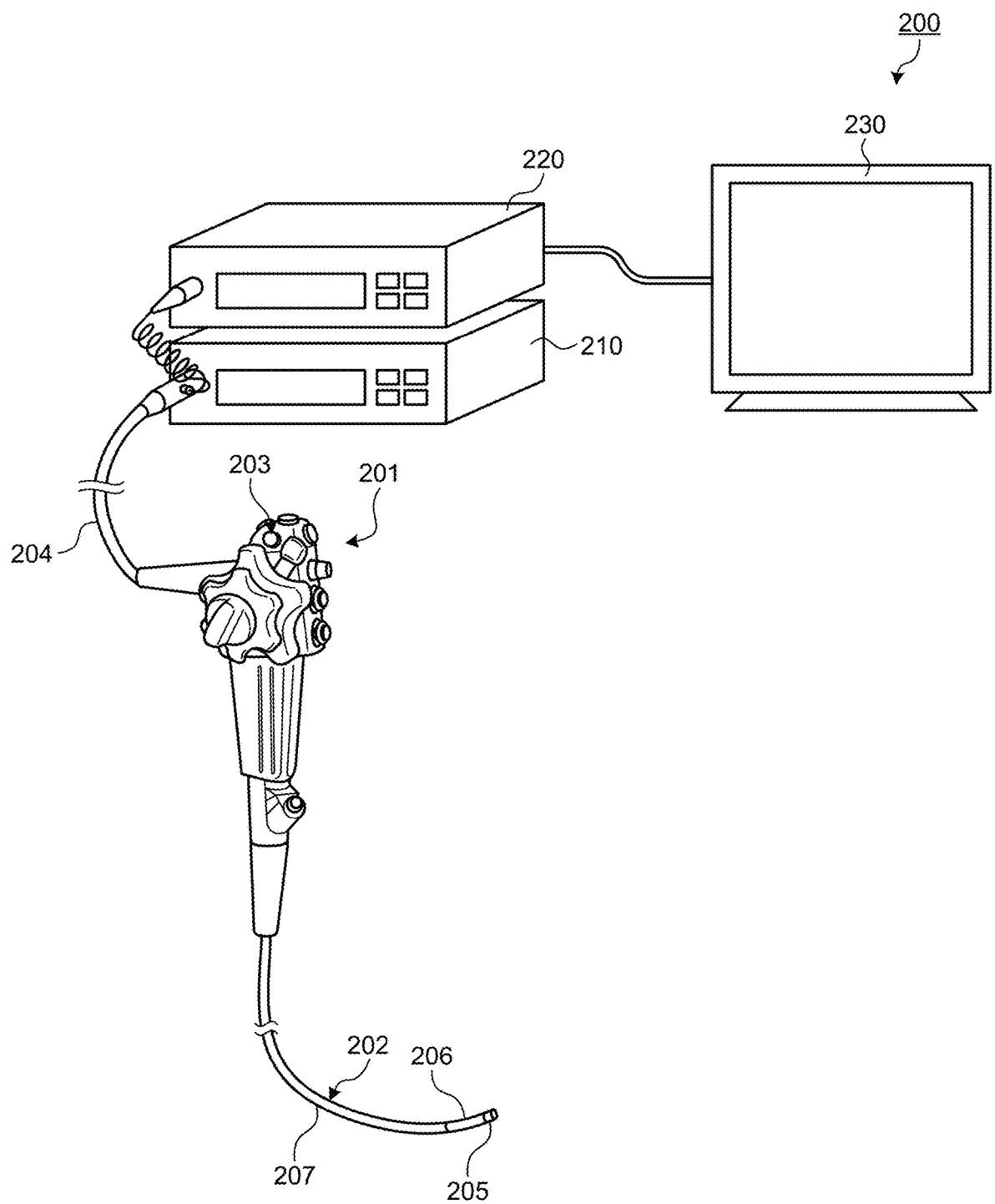
FIG. 20 is a view illustrating a schematic configuration of an endoscope device according to a second embodiment of the present invention.

Next, a second embodiment of the present invention is described. FIG. 20 is a view illustrating the schematic configuration of an endoscope device 200 according to the second embodiment of the present invention. In the above-described first embodiment, the description has been made with respect to the endoscope device 1 which uses the rigid endoscope as the endoscope 2. However, the present invention is not limited to such a case, and an endoscope device which uses a flexible endoscope may be adopted. In the second embodiment, the description is made by taking a case where an observation-side filter and an imaging unit are provided at a distal end of an insertion portion of the flexible endoscope as an example.

The endoscope device 200 includes: an endoscope 201 which captures an in-vivo image of an observed region by inserting an insertion portion 202 into a subject and generates an imaging signal; a light source device 210 which generates an illumination light to be emitted from a distal end of the endoscope 20; a control device 220 which applies a predetermined image processing to the imaging signal acquired by the endoscope 201 and controls an entire operation of the endoscope device 200 in a comprehensive manner; and a display device 230 which displays the in-vivo image to which the control device 22 applies image processing. The endoscope device 200 acquires an in-vivo image in a subject by inserting an insertion portion 202 in the subject such as a patient. The control device 220 has functions such as a signal processing unit 51 and an image processing unit 52 (including a filter detection unit 52a) described above.

The endoscope 201 includes: the insertion portion 202 which has flexibility and has an elongated shape; an operating unit 203 which is connected to a proximal end side of the insertion portion 202 and receives inputting of various of operation signals; and a universal code 204 which extends from the operating unit 203 in a direction different from an extending direction of the insertion portion 202 and incorporates various kinds of cables connected to the light source device 210 and the control device 220, respectively.

The insertion portion 202 includes: a distal end portion 205 which incorporates the imaging unit according to this embodiment; a curved portion 206 which is formed of a plurality of curved pieces and is freely bendable; and an elongated flexible tube portion 207 having flexibility which is connected to a proximal end side of the curved portion 206.

As the endoscope 201, any one of an endoscope having the above-described observation-side filter, an endoscope having no observation-side filter, or an endoscope where an observation-side filter is detachably mounted is connected to the control device 220. The observation-side filter is provided at a stage in front of the imaging unit, for example.

The light source device 210 is formed so as to switch a light emission made between an emission of a white light and an emission of a near-infrared excitation light. Specifically, the light source device 210 has either one of the configuration capable of emitting a white light and a special light by combining a halogen lamp and an illumination-side filter with each other or the configuration having an LED for emitting a white light and a semiconductor laser for emitting a near-infrared excitation light.

In the endoscope device 200 described above, in the same manner as the first embodiment and the modification, the filter detection unit 52a detects whether or not the observation-side filter is disposed in the endoscope 201. In the control device 220, the notification processing and the illumination light control are performed based on a detection result of the observation-side filter.

As described above, the endoscope device 200 which includes the flexible endoscope 201 may also acquire substantially the same manner of operation and advantageous effects as the above-described first embodiment.

Third Embodiment

Figure 21:
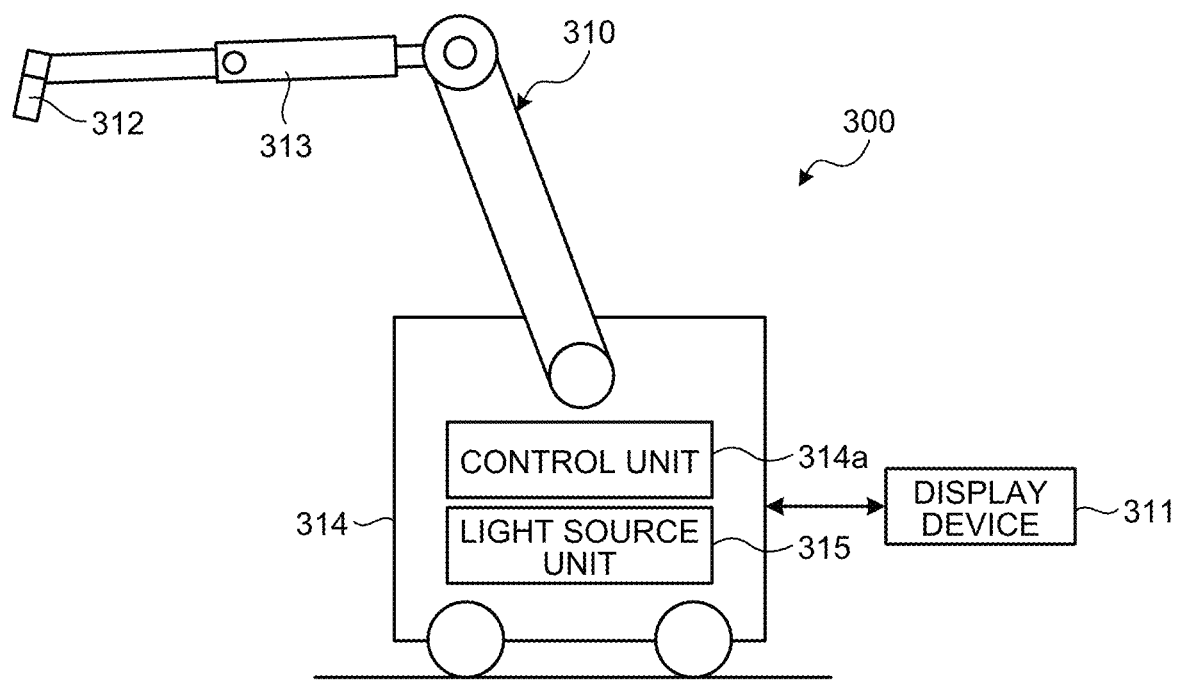
FIG. 21 is a view schematically illustrating an overall configuration of a surgical microscope system which is a medical observation system including a medical imaging device according to a third embodiment of the present invention.

Next, a third embodiment of the present invention is described. FIG. 21 is a view schematically illustrating an overall configuration of a surgical microscope system according to the third embodiment of the present invention which is a medical observation system including a medical imaging device. Although the description has been made by exemplifying the rigid or flexible endoscope in the above-described first and second embodiments, in the third embodiment, the description is made by taking a surgical microscope system (medical image acquisition system) having a function of imaging a predetermined viewing range in an enlarged manner and displaying an imaged image as an example.

A surgical microscope system 300 includes: a microscope device 310 which is a medical imaging device capable of obtaining an image for observing a subject by capturing; and a display device 311 which displays the image imaged by the microscope device 310. The display device 311 may also be formed integrally with the microscope device 310.

The microscope device 310 includes: a microscope unit 312 which captures an image of a minute part of a subject in an enlarged manner; a support portion 313 which is connected to a proximal end portion of the microscope unit 312 and includes an arm rotatably supporting the microscope unit 312; and a base portion 314 which holds a proximal end portion of the support portion 313 in a rotatable manner and is movable on a floor surface. The base portion 314 includes: a control unit 314a which controls an operation of the surgical microscope system 300, and a light source unit 315 which generates an illumination light which is irradiated to the subject from the microscope device 310. The control unit 314a has functions of the signal processing unit 51 and the image processing unit 52 (including the filter detection unit 52a) and the like described above. The base portion 314 may be formed so as to support the support portion 313 by being fixed to a ceiling, a wall surface, or the like instead of being movably placed on a floor surface.

The microscope unit 312 has a circular cylindrical shape, for example, and the above-described imaging unit 92 is disposed in the microscope unit 312. On a side surface of the microscope unit 312, a switch which receives inputting of an operation instruction for the microscope device 310 is provided. A cover glass for protecting the inside of the microscope unit 312 is provided on an aperture surface at a lower end portion of the microscope unit 312 (not illustrated).

In the microscope device 310, the microscope unit 312 may adopt any one of the configurations among the configuration which includes the observation-side filter, the configuration which includes no observation-side filter, and the configuration where the observation-side filter is detachably provided. The observation-side filter is provided at a stage in front of the imaging unit of the microscope unit 312, for example.

The light source unit 315 is formed so as to switch an emission of light between a white light and a near-infrared excitation light. Specifically, the light source unit 315 has either one of a configuration capable of emitting a white light and a special light by combining a halogen lamp and an illumination-side filter with each other, or a configuration having an LED for emitting a white light and a semiconductor laser for emitting a near-infrared excitation light.

A user such as a surgeon moves the microscope unit 312, performs zooming or switching an illumination light by operating various kinds of switches in a state where the user grasp the microscope unit 312. It is preferable that the microscope unit 312 be formed in a shape extending in an elongated manner in an observation direction such that the user may easily change the viewing direction by grasping the microscope unit 312. Accordingly, the shape of the microscope unit 312 may be a shape other than the circular cylindrical shape, and may be a polygonal columnar shape, for example.

In the control unit 314a, in the same manner as the first embodiment and the modifications, the filter detection unit 52a detects whether or not the observation-side filter is disposed in the microscope unit 312. The control unit 314a performs notification processing and an illumination light control based on a detection result of an observation-side filter.

As has been described heretofore, also in the surgical microscope system 300, substantially the same advantageous effects as the above-described first embodiment may be obtained.

Hereinbefore, the embodiment for carrying out the present invention is described. However, the present invention should not be limited to only the above-described embodiments. In the above-described embodiments, the description is made by assuming that the control device 5 performs the signal processing or the like. However, the signal processing or the like may be performed on a camera head 9 side.

INDUSTRIAL APPLICABILITY

As described above, the medical observation system according to the present invention is useful for detecting the presence or absence of a filter in the observation optical system while suppressing the increase of the scale of a circuit.

REFERENCE SIGNS LIST

1 ENDOSCOPE DEVICE
2, 2A, 2B ENDOSCOPE
3 IMAGING DEVICE
4 DISPLAY DEVICE
5 CONTROL DEVICE
6 LIGHT SOURCE DEVICE
7 LIGHT GUIDE
8 TRANSMISSION CABLE
9, 9A, 9B CAMERA HEAD
10, 10A INTERMEDIATE MEMBER
10A, 10B, 21F, 95 OBSERVATION-SIDE FILTER
51 SIGNAL PROCESSING UNIT
52 IMAGE PROCESSING UNIT
52A FILTER DETECTION UNIT
53 COMMUNICATION MODULE
54 INPUT UNIT
55 OUTPUT UNIT
56 CONTROL UNIT
57 MEMORY
61 LIGHT SOURCE UNIT
62 LIGHT SOURCE CONTROLLER
91 LENS UNIT
92 IMAGING UNIT
93 COMMUNICATION MODULE
94 CAMERA HEAD CONTROLLER

The invention claimed is:

1. A medical observation system comprising:
a camera head for use with a plurality of types of units of observation systems, the observation system configured to guide an illumination light to a subject and to guide an observation light from the subject, the camera head including an image sensor configured to receive the observation light from the observation system and generate an image signal; and
circuitry configured to:
apply signal processing to the image signal generated by the image sensor,
detect, based on a signal value in a first wavelength band included in a wavelength band of the observation light from the subject in the image signal, whether or not a filter is disposed on an optical path of the observation light, the filter being a filter that cuts the first wavelength band of the observation light over an entirety of the image sensor.

2. The medical observation system according to claim 1, wherein
the filter is insertable into and removable from the observation system.

3. The medical observation system according to claim 2, wherein the circuitry is further configured to
receive an instruction, and
perform detection processing of the filter when the instructions is a white balance adjustment processing instruction.

4. The medical observation system according to claim 3, wherein the circuitry is further configured to, based on a detection result, control a display and/or to output notification processing indicating that the filter is not provided when it is determined that the filter does not exist in the observation system.

5. The medical observation system according to claim 2, wherein the circuitry is further configured to, based on a detection result, control a display and/or to output notification processing indicating that the filter is not provided when it is determined that the filter does not exist in the observation system.

6. The medical observation system according to claim 2, further comprising
a light source configured to emit the illumination light.

7. The medical observation system according to claim 1, wherein the circuitry is further configured to
receive an instruction, and
perform detection processing of the filter when the instruction is a white balance adjustment processing instruction.

8. The medical observation system according to claim 7, wherein the circuitry is further configured to, based on a detection, control a display and/or output notification processing indicating that the filter is not provided when it is determined that the filter does not exist in the observation system.

9. The medical observation system according to claim 7, further comprising
a light source configured to emit the illumination light.

10. The medical observation system according to claim 1, further comprising
a control circuit configured to, based on a detection, control a display and/or perform notification processing indicating that the filter is not provided when it is determined that the filter does not exist in the observation system.

11. The medical observation system according to claim 10, further comprising
a light source configured to emit the illumination light.

12. The medical observation system according to claim 11, further comprising
a light source control circuit configured to control, based on a detection result, emission of the illumination light from the light source when it is determined that the filter does not exist in the observation system.

13. The medical observation system according to claim 1, further comprising
a light source configured to emit the illumination light.

14. The medical observation system according to claim 13, further comprising
a light source control circuit configured to control, based on a detection result, emission of the illumination light from the light source when it is determined that the filter does not exist in the observation system.

15. The medical observation system according to claim 1, on condition that the filter is in the observation system, signal processing further includes compensating for colors cut by the filter when generating a white light image.

16. The medical observation system according to claim 1, on condition that the filter does not exist in the observation system, signal processing sets a color mode to a normal white light image color mode.

17. The medical observation system according to claim 1, on condition that the filter is in the observation system, allow a fluorescence observation mode.

18. The medical observation system according to claim 1, wherein the circuitry is further configured to determine a type of unit of the observation system in use based on the presence or absence of the filter.

19. A medical control device, comprising:
circuitry configured to
detect, based on a signal value in a first wavelength band included in a wavelength band of an observation light from a subject of an image signal generated by an image sensor that receives the observation light from the subject that has been illuminated by an illumination light, the image sensor for use with a plurality of types of units of observation systems, whether or not a filter is disposed on an optical path the observation system directing the illumination light to the subject and the observation light from the subject, the filter being a filter that cuts the first wavelength band of the observation light over an entirety of the image sensor, and
apply signal processing to the image signal in accordance with whether or not the filter is present in the observation system.

20. The medical control device according to claim 19, wherein the circuitry is configured to set a color mode for signal processing the image signal in accordance with whether or not the filter is present in the observation system.

21. The medical control device according to claim 19, wherein the circuitry is further configured to determine a type of unit of the observation system in use based on the presence or absence of the filter.

22. A control device, comprising:
circuitry configured to
detect, based on a signal value in a first wavelength band included in a wavelength band of an observation light from a subject of an image signal generated by an image sensor that receives the observation light from the subject that has been illuminated by an illumination light, the image sensor for use with a plurality of types of units of observation systems, whether or not a filter that cuts the light first wavelength band of the observation light over an entirety of the image sensor is disposed on an optical path of the observation system directing the illumination light to the subject and the observation light from the subject, and
apply signal processing to the image signal in accordance with whether or not the filter is present in the observation system.

23. The control device according to claim 22, wherein the circuitry is further configured to determine a type of unit of the observation system in use based on the presence or absence of the filter.

* * * * *